US007511016B2

(12) United States Patent
Reutelingsperger

(10) Patent No.: US 7,511,016 B2
(45) Date of Patent: Mar. 31, 2009

(54) ANNEXINS, DERIVATIVES THEREOF, AND ANNEXIN-CYS VARIANTS, AS WELL AS THERAPEUTIC AND DIAGNOSTIC USES THEREOF

(75) Inventor: Chris Reutelingsperger, Maastricht (NL)

(73) Assignee: MosaMedix B.V., Kattendijke (NL)

( * ) Notice: Subject to any disclaimer, the term of this patent is extended or adjusted under 35 U.S.C. 154(b) by 541 days.

(21) Appl. No.: 10/886,262

(22) Filed: Jul. 7, 2004

(65) Prior Publication Data

US 2006/0009381 A1 Jan. 12, 2006

(51) Int. Cl.
*A61K 38/00* (2006.01)
(52) U.S. Cl. ...................................... 514/12
(58) Field of Classification Search ................. None
See application file for complete search history.

(56) References Cited

U.S. PATENT DOCUMENTS

| | | | | |
|---|---|---|---|---|
| 5,166,322 | A | * 11/1992 | Shaw et al. | 530/351 |
| 5,632,986 | A | * 5/1997 | Tait et al. | 424/94.64 |
| 5,834,196 | A | 11/1998 | Reutelingsperger | |
| 6,197,278 | B1 | 3/2001 | Blankenberg et al. | |
| 6,312,694 | B1 | * 11/2001 | Thorpe et al. | 424/178.1 |
| 6,323,313 | B1 | 11/2001 | Tait et al. | |
| 7,015,310 | B2 | * 3/2006 | Remington et al. | 530/350 |
| 2002/0083888 | A1 | * 7/2002 | Zehnder et al. | 117/69 |
| 2002/0192162 | A1 | * 12/2002 | Green | 424/9.4 |
| 2002/0192721 | A1 | * 12/2002 | Rizzuto et al. | 435/7.9 |

FOREIGN PATENT DOCUMENTS

| WO | WO 00/10673 A1 | 3/2000 |
|---|---|---|
| WO | WO 03/103577 A2 | 12/2003 |

OTHER PUBLICATIONS

Bork et al. Go hunting in sequence databases but watch out for the traps. Trends in Genetics. 12(10): 425-427, 1996.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Skolnick et al. From genes to protein structure and function: novel applications of computational approaches in the genomic era. Trends in Biotech 18(1): 34-39, 2000.*
Brenner, S.E. Errors in genome function. Trends in Genetics 15(4): 132-133, 1999.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Smith et al. The challenges of genome sequence annotation or "The devil is in the details". Nature Biotech 15: 1222-1223, 1997.*

Andree H.A., Reutelingsperger C.P., Hauptmann A., Hemker H.C., Hermens W.T., and Willems G.M., *Binding of vascular anticoagulant alpha (VAC alpha) to planar phospholipid bilayers*, J Biol Chem 265:4923-4928 (1990).
Blackwood, R. A., and Ernst, J. D. (1990). Characterization of Ca2(+)- dependent phospholipid binding, vesicle aggregation and membrane fusion by annexins. Biochem J 266, 195-200.
Blankenberg, F. G., Katsikis, P. O., Tait, J. F., Davis, R. E., Naumovski, L., Ohtsuki, K., Kopiwoda, S., Abrams, M. J., Darkes, M., Robbins, R. C., Maecker, H. T., and Strauss, H. W., *In vivo detection and imaging of phosphatidylserine expression during programmed cell death*, Proc Natl Acad Sd U S A 95, 6349-54 (1998).
Capila, I., Hernaiz, M. J., Mo, Y. D., Mealy, T. A., Campos, B., Dedman, J. R.. Linhardt, R. J., and Seaton, B. A. (2001). Annexin V—heparin oligosaccharide complex suggests heparan sulfate—mediated assembly on cell surfaces. Structure (Camb) 9, 57-64.
Casciola-Rosen, L., Rosen, A., Petri, M., and Schlissel, M., Surface blebs on apoptotic cells are sites of enhanced procoagulant activity: Implications for coagulation events and antigenic spread in systemic lupus erythematosus, Proc. Natl.Acad. Sd. U.S.A. 93, 1624-1629 (1996).
Dachary-Prigeflt, J., Toti, F., Satta, N., Pasquet, J. M., Uzan, A., and Freyssiriet, J. M., PhysiopathologiCal significance of catalytic phospholipids in the generation of thrombin, Seminars in Thrombosis and Hemostasis 22, 157-164 (1996).
Dumont, E. A., Reutelingsperger, C. P., Smits, J. F., Daemen, M. J., Doevendans, P. A., Wellens, H. J., and Hofstra, L., *Real-time imaging of apoptotic cell-membrane changes at the single-cell level in the beating murine heart*, Nat Med 7, 1352-5 (2001).
Geisow, M. J., Fritsche, U., Hexham, J. M., Dash, B., and Johnson, T., *A consensus amino-acid sequence repeat in Torpedo and mammalian Ca2+-dependent membrane-binding proteins*, Nature 320, 636-8 (1986).
Goth, S. R., and Stephens, R. S., *Rapid, transient phosphatidylserifle externalization induced in host cells by infection with Chiamydia spp*, Infect Immun 69, 1109-19 (2001).
Hammill, A. K., Uhr, J. W., and Scheuermanfl, A. H., *Annexin V staining due to loss of membrane asymmetry can be reversible and precede commitment to apoptotic death*, Experimental Cell Research 251, 16-21 (1999).

(Continued)

*Primary Examiner*—Lorraine Spector
*Assistant Examiner*—Elly-Gerald Stoica
(74) *Attorney, Agent, or Firm*—Foley & Lardner LLP

(57) ABSTRACT

The present invention provides methods and compositions for the treatment, diagnosis, and prevention of diseases, such as neoplastic diseases, neurodegenerative diseases, cardiovascular diseases, autoimmune diseases, and inflammatory diseases. The methods include the administration of pharmaceutical complexes comprising annexins coupled to pharmaceutical compounds or carriers to subjects. The present invention also provides methods and compositions for delivering therapeutic compounds into the diseased cells of a subject either to kill them, such as tumor cells, or to rescue them, such as cardiomyocytes and neurons. The compositions include annexins, annexin variants, derivatives thereof, and complexes thereof.

25 Claims, 10 Drawing Sheets

OTHER PUBLICATIONS

Hamon, Y., Broccardo, C., Chambenoit, O., Luciani, M. F., Toti, F., Chaslin, S., Freyssinet, J. M., Devaux, P. F., NcNeish, J., Marguet, D., and Chimini, G., *ABC1 promotes engulfment of apoptotic cells and transbilayer redistribution of phosphatidylserine*, Nat Cell Biol 2, 399-406 (2000).

Hofstra, L., Dumont, E. A., Thimister, P. W., Heidendal, G. A., DeBruine, A. P.. Elenbaas, T. W., Boersma, H. H., van Heerde, W. L., and Aeutelingsperger, C. P., In vivo *detection of apoptosis in an intracardiac tumor*, Jama 285, 1841-2 (2001).

Hofstra, L., Liem, I. H., Dumont, E. A., Boersma, H. H., van Heerde, W. L., Doevendans, P. A., DeMuinck, E., Wellens, H. J. J., KKemerink, G. J., Reutelingsperger, C. P. M., and Heidendal, G. A., *Visualisation of cell death in vivo in patients with acute myocardial infarction*, Lancet 356, 209-212 (2000).

Huber, A., Romisch, J., and Paques, E. P., *The crystal and molecular structure of human annexin V, an anticoagulant protein that binds to calcium and membranes*, EMBO J 9, 3867-74 (1990a).

Huber, R., Schneider, M., Mayr, I., Romisch, J., and Paques, E. P., *The calcium binding sites in human annexin V by crystal structure analysis at 2.0 A resolution. Implications for membrane binding and calcium channel activity*, FEBS Lett 275, 15-21 (1990b).

Leist, M., and Jaattela, M., *Four deaths and a funeral: from caspases to alternative mechanisms*, Nat Rev Mol Cell Blot 2, 589-98 (2001).

Mallat, Z., Benamer, H., Hugel, B., Benessiano, J., Steg, P. G., Freyssinet, J. M., and Tedgui, A., *Elevated levels of shed membrane microparticles with procoagulant potential in the peripheral circulating blood of patients with acute coronary syndromes*, Circulation 101, 841-843 (2000).

Mallat, Z., Hugel, B., Ohan, J., LesEche, G., Freyssinet, J. M., and Tedgui, A., *Shed membrane microparticles with procoagulant potential in human atherosclerotic plaques: a role for apoptosis in plaque thrombogenicity*, Circulation 99, 348-53 (1999).

Maurer-Fogy, I., Reutelingsperger, C. P., Pieters, J., Bodo, G., Stratowa, C., and Hauptmann, R., *Cloning and expression of cDNA for human vascular anticoagulant, a Ca2+-dependent phospholipid-binding protein*, Eur. J Biochem. 174, 585-92 (1988).

Narula, J., Ada, E. R., Narula, N., Samuels, L. E., Fyfe, B., Wood, D., Fitzpatrick, J. M., Raghunath, P. N., Tornaszewski, J. E., Kelly, C., Steinmetz, N., Green, A., Tait, J. F., Leppo, J., Blankenberg, F. G., Jam, D., and Strauss, H. W., *Annexin-V imaging for noninvasive detection of cardiac allograft rejection*, Nat Med 7, 1347-52 (2001).

Nieuwland, R., Berckmans, R. J., RotteveelEijkman, A. C., Maquelin, K. N., Roozendaal, K. J., Jansen, P. G. M., tenHave, K., Eijsman, L., Hack, C. E., and Sturk, A., *Cell-derived microparticles generated in patients during cardiopulmonary bypass are highly procoagulant*, Circulation 96, 3534-3541 (1997).

Oling, F., Bergsma Schutter, W., and Brisson, A., *Trimers, dimers of trimers, and trimers of trimers are common building blocks of annexin a5 two-dimensional crystals*, J Struct. Bid 133, 55-63 (2001).

Oling, F., Santos, J. S., Govorukhina, N., Mazeres Dubut, C., Bergsma Schutter, W., Oostergetel, G., Keegstra, W., Lambert, O., Lewit Bentley, A., and Brisson, A. (2000). Structure of membrane-bound annexin A5 trimers: a hybrid cryo-EM—X-ray crystallography study. J Mcl Biol 304, 561-73.

Satta, N., Toti, F., Feugeas, O., Bohbot, A., Dacharyprigent, J., Eschwege, V., Hedman, H., and Freyssinet, J. M., *Monocyte vesiculation is a possible mechanism for dissemination of membrane-associated procoagulant activities and adhesion molecules after stimulation by lipopolysaccharide*, Journal of Immunology 1 53, 3245-3255 (1994).

Savill, J., and Fadok, V. (2000). Corpse clearance defines the meaning of cell death. Nature 407, 784-8.

Seaton, B. A., and Dedman, J. A., *Annexins*, Biometals 11, 399-404 (1998).

Tanaka, K.. Elnaga, K., Tsuchiyama, H., Tait, J. F., and Fujikawa, K. (1996). Preparation and characterization of a disulfide-linked bioconjugate of annexin V with the B-chain of urokinase: An improved fibrinolytic agent targeted to phosphatidylserine-containing thrombi. Biochemistry 35, 922-929.

Tait, J. F., Brown, D. S., Gibson, D. F., Blankenberg, F. G., and Strauss, H. W. (2000). Development and characterization of annexin V mutants with endogenous chelation sites for (99m)Tc. Bioconjug Chem 11, 918-25.

Tait, J. F., Engelhardt, S., Smith, C., and Fujikawa, K., *Prourokinase-annexin V chimeras—Construction, expression, and characterization of recombinant proteins*, Journal of Biological Chemistry 270, 21594-21599 (1995).

Tait, J. F., and Smith, C. (1991). Site-specific mutagenesis of annexin V: role of residues from Arg-200 to Lys-207 in phospholipid binding. Arch Biochem Blophys 288, 141-4.

Van den Eijnde, S. M., Bosharl, L., Reutelingsperger, C. P. M., DeZeeuw, C. I., and VermeijKeers, C., *Phosphatidylserine plasma membrane asymmetry in vivo: A pancellular phenomenon which alters during apoptosis*, Cell Death Differentiation 4, 311-316 (1997).

Van den Eijnde, S. M. Luijsterburg, A. J., Boshart, L., De Zeeuw, C. I., van Dierendonck, J. H., Reutelingsperger, C. P., and Vermeij Keers, C. (1997). In situ detection of apoptosis during embryogenesis with annexin V: from whole mount to ultrastructure. Cytometry 29, 313-320.

Van den Eijnde, S. M., van den Hoff, M. J., Reutelingsperger, C. P., van Heerde, W. L., Henflirig, M. E., Vermeij-Keers, C., Schutte, B., Borgers, M., and Raniaekers, F. C., *Transient expression of ptiosphatidylserine at cell-cell contact areas is required for myotube formation*, J Cell Sci 114, 3631-42 (2001).

Van Engeland, M., Nietand, L. J. W., Rarnaekers, F. C. S., Schutte, B., and Reutelingsperger, C. P. M., *Annexin V-affinity assay: A review on an apoptosis detection system based on phosphatidylserine exposure*, Cytometry 31 (1), 1-9 (1998).

Van Heerde, W. L., Degroot, P. G., and Reutelingsperger, C. P. M., *The complexity of the phospholipid binding protein annexin V*, Thromb. Haemost. 73, 172-179 (1995).

Vermes, I., Haanen, C., Steftensnakken, H., and Reutelingsperger, C. (1995). A novel assay for apoptosis—Flow cytometric detection of phosphatidylserine expression on early apoptotic cells using fluorescein labelled Annexin V. Journal of Immunological Methods 184, 39-51.

Zwaal, R. F., and Schroit, A. J., Pathophysiologic implications of membrane phospholipid asymmetry in blood cells, Blood 89, 1121-32 (1997).

Aupeix et al., "The Significance of Shed Membrane Particles during Programmed Cell Death In Vitro, and In Vivo, in HIV-1 Infection," *J. Clin. Invest.*, Apr. 1997, pp. 1546-1554, vol. 99, No. 7, The American Society for Clinical Investigation, Inc.

Fadok et al., "Exposure of Phosphatidylserine on the Surface of Apoptotic Lymphocytes Triggers Specific Recognition and Removal by Macrophages," *The Journal of Immunology*, Apr. 1, 1992, pp. 2207-2216, vol. 148, The American Association of Immunologists.

Kasina, S., et al, "Preformed Chelate TC-99M Radiolabeling of R-Annexin V for Arterial Thromnus Imaging," *Journal of Nuclear Medicine*, Society of Nuclear Medicine, Reston, Va., vol. 37, No. 5, suppl., May 1996, p. 29.

Budisa, N., et al., "Residue-specific bioincorporation of non-natural, biologically active amino acids into proteins as possible drug carriers: Structure and stability of the per-thiaproline mutant of annexin V," *Proceedings of the National Academy of Sciences of USA*, National Academy of Science, Washington, DC, vol. 95, 1998, pp. 455-459.

Kenis, Heidi, et al., "Cell surface-expressed phosphatidylserine and annexin A5 open a novel portal of cell entry," *The Journal of Biological Chemistry*, vol. 279, No. 50, Dec. 10, 2004, pp. 52623-52629.

Heerde, Van W. L., et al., "Binding of Recombinant Annexin V to Endothelial Cells: Effect of Annexin V Binding on Endothelial-Cell-Mediated Thrombin Formation," *Biochemical Journal*, vol. 302, no. Part 1, Portland Press, London, GB, Aug. 15, 1994, pp. 305-312.

Huber, R., et al., "Crystal and Molecular Structure of Human Annexin V Alter Refinement Implications for Structure Membrana Binding and Ion Channel Formation of the Annexin Family of Proteins", *Journal of Molecular Biology*, vol. 223, No. 3, 1992, pp. 683-704.

* cited by examiner

Figure 1. SEQ ID NO: 1 – Annexin A5/Cys315

| 10 AQVLRGTVTD | 20 FPGFDERADA | 30 ETLRKAMKGL | 40 GTDEESILTL |
|---|---|---|---|
| 50 LTSRSNAQRQ | 60 EISAAFKTLF | 70 GRDLLDDLKS | 80 ELTGKFEKLI |
| 90 VALMKPSRLY | 100 DAYELKHALK | 110 GAGTNEKVLT | 120 EIIASRTPEE |
| 130 LRAIKQVYEE | 140 EYGSSLEDDV | 150 VGDTSGYYQR | 160 MLVVLLQANR |
| 170 DPDAGIDEAQ | 180 VEQDAQALFQ | 190 AGELKWGTDE | 200 EKFITIFGTR |
| 210 SVSHLRKVFD | 220 KYMTISGFQI | 230 EETIDRETSG | 240 NLEQLLLAVV |
| 250 KSIRSIPAYL | 260 AETLYYAMKG | 270 AGTDDHTLIR | 280 VMVSRSEIDL |
| 290 FNIRKEFRKN | 300 FATSLYSMIK | 310 GDTSGDYKKA | 319 LLLLCGEDD |

Figure 2. SEQ ID NO: 2 – Annexin A5/Ser315

| 10<br>AQVLRGTVTD | 20<br>FPGFDERADA | 30<br>ETLRKAMKGL | 40<br>GTDEESILTL |
|---|---|---|---|
| 50<br>LTSRSNAQRQ | 60<br>EISAAFKTLF | 70<br>GRDLLDDLKS | 80<br>ELTGKFEKLI |
| 90<br>VALMKPSRLY | 100<br>DAYELKHALK | 110<br>GAGTNEKVLT | 120<br>EIIASRTPEE |
| 130<br>LRAIKQVYEE | 140<br>EYGSSLEDDV | 150<br>VGDTSGYYQR | 160<br>MLVVLLQANR |
| 170<br>DPDAGIDEAQ | 180<br>VEQDAQALFQ | 190<br>AGELKWGTDE | 200<br>EKFITIFGTR |
| 210<br>SVSHLRKVFD | 220<br>KYMTISGFQI | 230<br>EETIDRETSG | 240<br>NLEQLLLAVV |
| 250<br>KSIRSIPAYL | 260<br>AETLYYAMKG | 270<br>AGTDDHTLIR | 280<br>VMVSRSEIDL |
| 290<br>FNIRKEFRKN | 300<br>FATSLYSMIK | 310<br>GDTSGDYKKA | 319<br>LLLLSGEDD |

Figure 3a. SEQ ID NO: 3 – Annexin A5/Ser315/Cys5

| 10<br>AQVLCGTVTD | 20<br>FPGFDERADA | 30<br>ETLRKAMKGL | 40<br>GTDEESILTL |
|---|---|---|---|
| 50<br>LTSRSNAQRQ | 60<br>EISAAFKTLF | 70<br>GRDLLDDLKS | 80<br>ELTGKFEKLI |
| 90<br>VALMKPSRLY | 100<br>DAYELKHALK | 110<br>GAGTNEKVLT | 120<br>EIIASRTPEE |
| 130<br>LRAIKQVYEE | 140<br>EYGSSLEDDV | 150<br>VGDTSGYYQR | 160<br>MLVVLLQANR |
| 170<br>DPDAGIDEAQ | 180<br>VEQDAQALFQ | 190<br>AGELKWGTDE | 200<br>EKFITIFGTR |
| 210<br>SVSHLRKVFD | 220<br>KYMTISGFQI | 230<br>EETIDRETSG | 240<br>NLEQLLLAVV |
| 250<br>KSIRSIPAYL | 260<br>AETLYYAMKG | 270<br>AGTDDHTLIR | 280<br>VMVSRSEIDL |
| 290<br>FNIRKEFRKN | 300<br>FATSLYSMIK | 310<br>GDTSGDYKKA | 319<br>LLLLSGEDD |

Figure 3b. SEQ ID NO: 4 – Annexin A5/Ser315/Cys7

| 10<br>AQVLRGCVTD | 20<br>FPGFDERADA | 30<br>ETLRKAMKGL | 40<br>GTDEESILTL |
|---|---|---|---|
| 50<br>LTSRSNAQRQ | 60<br>EISAAFKTLF | 70<br>GRDLLDDLKS | 80<br>ELTGKFEKLI |
| 90<br>VALMKPSRLY | 100<br>DAYELKHALK | 110<br>GAGTNEKVLT | 120<br>EIIASRTPEE |
| 130<br>LRAIKQVYEE | 140<br>EYGSSLEDDV | 150<br>VGDTSGYYQR | 160<br>MLVVLLQANR |
| 170<br>DPDAGIDEAQ | 180<br>VEQDAQALFQ | 190<br>AGELKWGTDE | 200<br>EKFITIFGTR |
| 210<br>SVSHLRKVFD | 220<br>KYMTISGFQI | 230<br>EETIDRETSG | 240<br>NLEQLLLAVV |
| 250<br>KSIRSIPAYL | 260<br>AETLYYAMKG | 270<br>AGTDDHTLIR | 280<br>VMVSRSEIDL |
| 290<br>FNIRKEFRKN | 300<br>FATSLYSMIK | 310<br>GDTSGDYKKA | 319<br>LLLLSGEDD |

Figure 3c. SEQ ID NO: 5 – Annexin A5/Ser315/Cys9

| 10<br>AQVLRGTVCD | 20<br>FPGFDERADA | 30<br>ETLRKAMKGL | 40<br>GTDEESILTL |
|---|---|---|---|
| 50<br>LTSRSNAQRQ | 60<br>EISAAFKTLF | 70<br>GRDLLDDLKS | 80<br>ELTGKFEKLI |
| 90<br>VALMKPSRLY | 100<br>DAYELKHALK | 110<br>GAGTNEKVLT | 120<br>EIIASRTPEE |
| 130<br>LRAIKQVYEE | 140<br>EYGSSLEDDV | 150<br>VGDTSGYYQR | 160<br>MLVVLLQANR |
| 170<br>DPDAGIDEAQ | 180<br>VEQDAQALFQ | 190<br>AGELKWGTDE | 200<br>EKFITIFGTR |
| 210<br>SVSHLRKVFD | 220<br>KYMTISGFQI | 230<br>EETIDRETSG | 240<br>NLEQLLLAVV |
| 250<br>KSIRSIPAYL | 260<br>AETLYYAMKG | 270<br>AGTDDHTLIR | 280<br>VMVSRSEIDL |
| 290<br>FNIRKEFRKN | 300<br>FATSLYSMIK | 310<br>GDTSGDYKKA | 319<br>LLLLSGEDD |

Figure 3d. SEQ ID NO: 6 – Annexin A5/Ser315/Cys11

| 10 AQVLRGTVTD | 20 CPGFDERADA | 30 ETLRKAMKGL | 40 GTDEESILTL |
|---|---|---|---|
| 50 LTSRSNAQRQ | 60 EISAAFKTLF | 70 GRDLLDDLKS | 80 ELTGKFEKLI |
| 90 VALMKPSRLY | 100 DAYELKHALK | 110 GAGTNEKVLT | 120 EIIASRTPEE |
| 130 LRAIKQVYEE | 140 EYGSSLEDDV | 150 VGDTSGYYQR | 160 MLVVLLQANR |
| 170 DPDAGIDEAQ | 180 VEQDAQALFQ | 190 AGELKWGTDE | 200 EKFITIFGTR |
| 210 SVSHLRKVFD | 220 KYMTISGFQI | 230 EETIDRETSG | 240 NLEQLLLAVV |
| 250 KSIRSIPAYL | 260 AETLYYAMKG | 270 AGTDDHTLIR | 280 VMVSRSEIDL |
| 290 FNIRKEFRKN | 300 FATSLYSMIK | 310 GDTSGDYKKA | 319 LLLLSGEDD |

Figure 4. SEQ ID NO: 7 – Annexin A5/Ser315/Cys2

| 10<br>ACVLRGTVTD | 20<br>FPGFDERADA | 30<br>ETLRKAMKGL | 40<br>GTDEESILTL |
|---|---|---|---|
| 50<br>LTSRSNAQRQ | 60<br>EISAAFKTLF | 70<br>GRDLLDDLKS | 80<br>ELTGKFEKLI |
| 90<br>VALMKPSRLY | 100<br>DAYELKHALK | 110<br>GAGTNEKVLT | 120<br>EIIASRTPEE |
| 130<br>LRAIKQVYEE | 140<br>EYGSSLEDDV | 150<br>VGDTSGYYQR | 160<br>MLVVLLQANR |
| 170<br>DPDAGIDEAQ | 180<br>VEQDAQALFQ | 190<br>AGELKWGTDE | 200<br>EKFITIFGTR |
| 210<br>SVSHLRKVFD | 220<br>KYMTISGFQI | 230<br>EETIDRETSG | 240<br>NLEQLLLAVV |
| 250<br>KSIRSIPAYL | 260<br>AETLYYAMKG | 270<br>AGTDDHTLIR | 280<br>VMVSRSEIDL |
| 290<br>FNIRKEFRKN | 300<br>FATSLYSMIK | 310<br>GDTSGDYKKA | 319<br>LLLLSGEDD |

Figure 5A
Jurkat cell population profile before the treatment with Annexin A5-Cys2-beads
Scatter pattern of the cell population
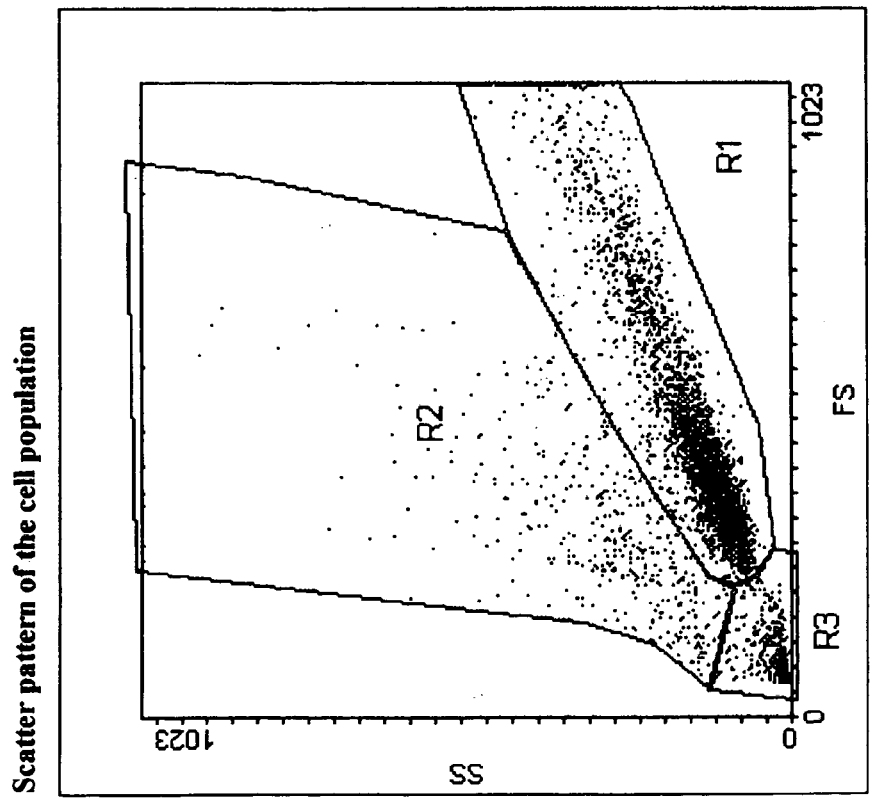
Cells with surface expression of PtdSer
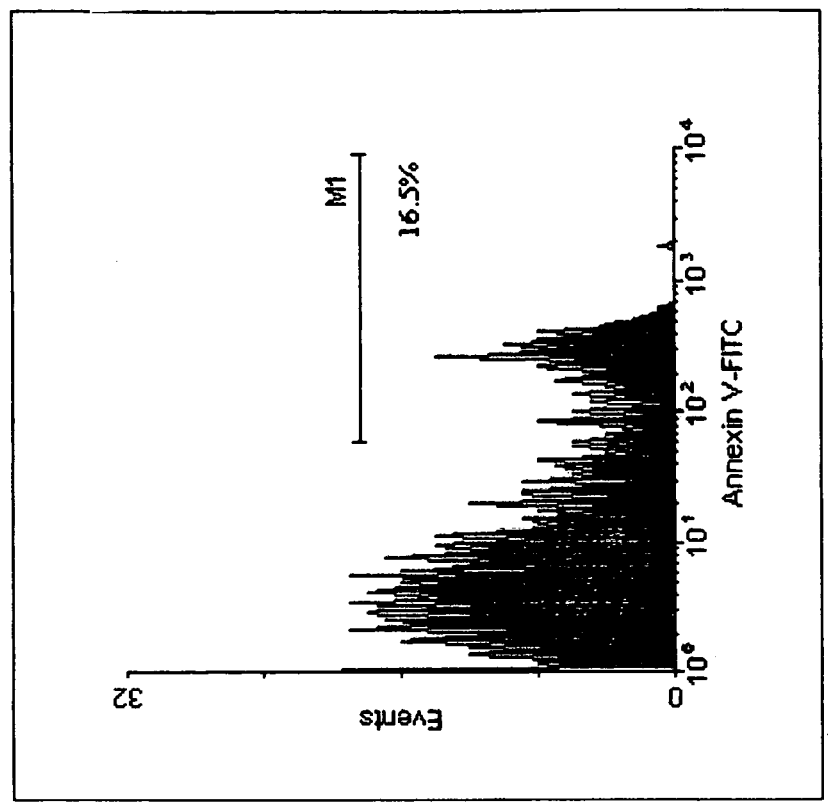

Figure 5B
Jurkat cell population profile after being depleted with Annexin A5-Cys2-beads
Scatter pattern of the cell population
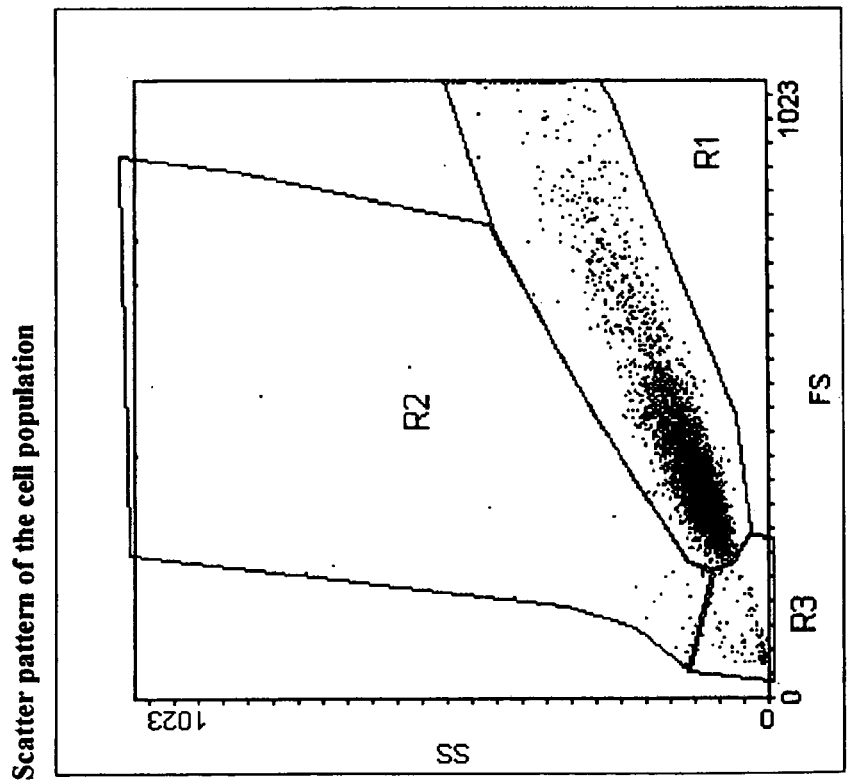
Cells with surface expression of PtdSer
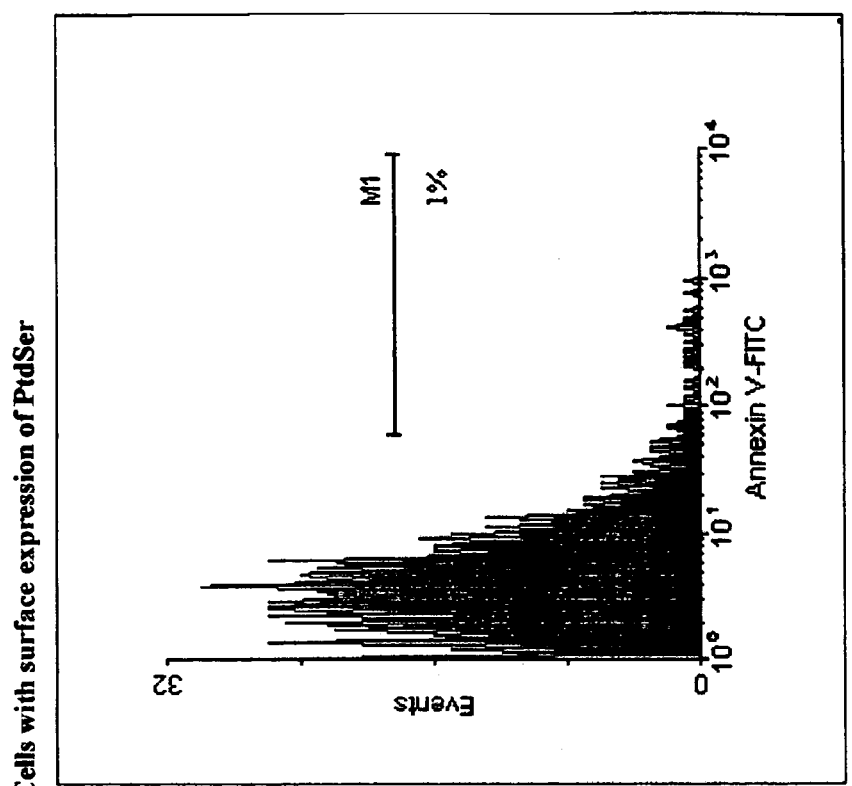

Figure 5C
Jurkat cell population profile that bound to the Annexin A5-Cys2-beads and was released with EDTA
Scatter pattern of the cell population
Cells with surface expression of PtdSer
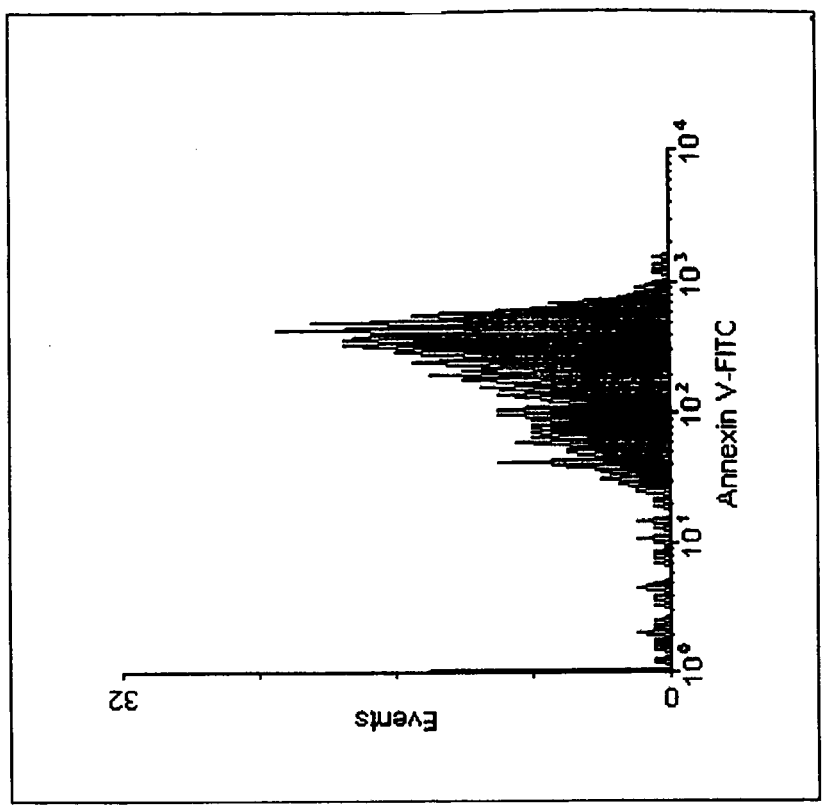
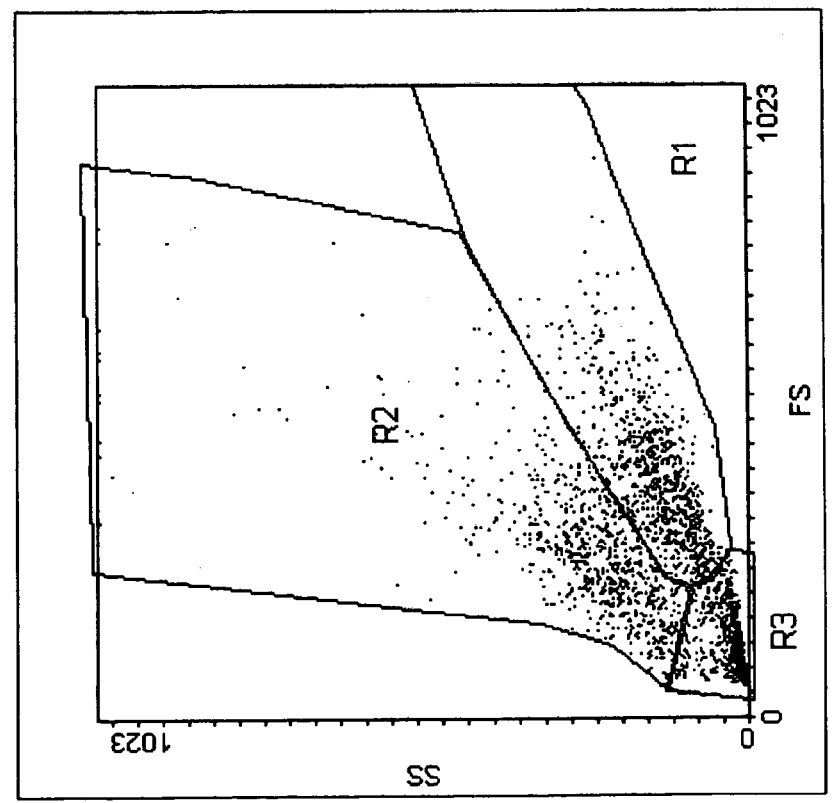

ANNEXINS, DERIVATIVES THEREOF, AND ANNEXIN-CYS VARIANTS, AS WELL AS THERAPEUTIC AND DIAGNOSTIC USES THEREOF

CROSS-REFERENCE TO RELATED PATENT APPLICATIONS

None.

BACKGROUND OF THE INVENTION

The present invention relates generally to the field of annexins. More particularly, it relates to compositions and methods for treating and diagnosing a subject by delivering compounds to a specified target using annexins, variants of annexins, and derivatives thereof.

Pharmacological and genetic treatments of diseases are based on the delivery of pharmacologically active compounds to diseased cells where the compounds act preferably intracellularly. Current therapeutic treatments employ systemic delivery of a drug, where the drug circulates through the entire body before reaching its desired target. This method of drug delivery results in systemic dilution of the compound. As a result, a patient requires higher concentrations of the drug to achieve the favored therapeutic efficacy. Higher drug concentrations naturally increase any undesired toxic side-effects of the pharmacologically active compounds. In addition, higher concentrations generally increase the cost of any drug.

To circumvent these problems regional drug delivery systems have been designed ranging from local applications to drug targeting. Regional delivery, however, is often insufficient because it does not ensure delivery into a targeted cell. In order to act efficiently, most drugs, such as chemotherapeutics and photodynamic agents, must enter a diseased cell. Several systems have been described that may be used to deliver compounds to a cell.

Cell-Penetrating Peptides or Protein Transduction Domains

Cell-Penetrating Peptides ("CPP") or Protein Transduction Domains ("PTD") form a class of peptides that are able to cross the plasma membranes of eucaryotic cells, (Lindgren, et al., Trends Pharmacol. Sci. 21:99-103 (2000)). Most CPP/PTDs are derived from larger proteins of viral origin. CPP/PTDs can also be engineered by design (U.S. Pat. No. 6,495,663). The mechanism by which CPP/PTDs translocate over the membrane is not entirely understood but it appears to be energy-independent. The potential use of CPP/PTDs in drug delivery has been recognized and examples of conjugates between CPP/PTDs and cargo such as small chemical entities, peptides, and proteins have been published (Schwarze, et al., Trends Pharmacol. Sci. 21:45-48 (2000); U.S. Pat. No. 6,472,507). The drawback of CPP/PTDs is their lytic activity at high concentrations (Scheller, et al., J. Pept. Sci. 5:185-94 (1999)). Additionally, CPP/PTDs do not have a targeting capability and do not discriminate between healthy and diseased cells. Hence, the toxic side-effects of pharmacological compounds are not diminished by their conjugation to CPP/PTDs. Rather, complexes formed from CPP or PTD and a pharmacological compound will enter both healthy and diseased cells. Targeting functionality has been attempted by conjugating CPP/PTDs to antibodies specific for antigens in tumors. The disadvantage of this approach, however, is that the targeting function of the antibody deteriorates as a result of the conjugation to the CPP/PTDs (Niesner, et al., Bioconjug Chem. 13:729-36 (2002)).

Ligands for Plasma Membrane Receptors.

Several pinocytic pathways have been described through which cells are able to internalize compounds from the environment. One of the pinocytic pathways comprises the receptor-ligand mediated endocytosis (Conner, et al., Nature 422: 37-44 (2003)). When the ligand binds to the receptor, the whole complex is internalized in small intracellular vesicles, which will travel through the cell depending on the receptor-ligand complex involved. This pathway can be employed to bring drugs into a cell through coupling the drug or the drug transporting vehicle such as liposomes to a ligand specific for surface receptors that show endocytosis upon ligation. Examples of such ligands that induce internalization are ligands for the hFGF-receptor (U.S. Pat. No. 6,551,618), ligands for the asialoglycoprotein receptor (U.S. Pat. No. 5,885,968), and ligands for the transferring receptor (U.S. Pat. Nos. 6,511,967, 5,154,924, Qian, et al., Pharmacol. Rev. 54:561-87 (2002)). This type of internalization does not, in most cases, achieve an optimal targeting function for drug delivery. Moreover, recent data show that internalization via the receptor-ligand pathway may suppress the pharmacological action of the internalized drug (Sato, et al., Pharm. Res. 19:1736-44 (2002)).

One compound that can be used as a targeting agent and capturing agent is Annexin A5. In order to detect Annexin A5 bound to the surface, it has been conjugated to reporter compounds. In the past, Annexin A5 conjugates have been prepared by reacting reporter compounds with amino and hydroxyl groups present in the Annexin A5 molecule. Annexin A5, however, has more than one amino group and more than one hydroxyl group. As a result, chemical coupling with these functional groups yields mixtures of different stoichiometric complexes of Annexin A5 and the reporter compound. The outcome of these coupling procedures is random and contains complexes that lack the ability to bind to aminophospholipids because a set of the reacting amino acids are involved in phospholipid binding. These problems impair the quality of the Annexin A5 conjugates. In order to improve quality, the mixture of Annexin A5 conjugate has been separated by additional purification techniques.

In an attempt to improve Annexin A5 for conjugation, the single sulfhydryl group in Annexin A5, which is provided by a cysteine residue at position 315, has been coupled with a single chain urokinase in an attempt to remedy the problems with the amino and hydroxyl groups discussed above (U.S. Pat. No. 5,632,986). The complexes of Annexin A5 and urokinases target the urokinases to intravascular sites in order to the increase local fibrinolytic activity. The sulfhydryl group, however, is buried inside the molecule and urea induced unfolding of Annexin A5 is required to expose the sulfhydryl group to the surface of the protein. This procedure is used to allow conjugation to occur. Subsequent refolding of the Annexin A5, however, is required to regain the phospholipid binding capabilities of Annexin A5. Refolding procedures are not one hundred percent effective and typically generate an ineffective mixture of binding and non-binding annexin molecules.

U.S. Pat. No. 5,632,986 also describes the chemical introduction of multiple sulfhydryl groups with sulfosuccinimidyl 4-(N-maleimidomethyl)cyclohexane-1-carboxylate ("SMCC") into the Annexin A5 molecule for conjugation purposes. This procedure generates the same problems experienced with the procedure employed for the amino and hydroxyl groups discussed above. U.S. Pat. No. 5,632,986 further describes a variant of Annexin A5 with an extended N-terminus of ten amino acids comprising one cysteine residue in order to allow conjugation to a reporter compound.

These variants have 329 amino acids of which two are cysteines. These variants may pose the problem of forming intramolecular disulfide bridges, thereby impairing the Annexin A5's ability to bind to phospholipids.

Bioactive compounds have also been conjugated to Annexin A5 by recombinant preparations of chimeras of Annexin A5 and the bioactive compounds (Tait, et al., Journal of Biological Chemistry 270:21594-99 (1995), U.S. Pat. Nos. 5,632,986). 6,323,313 describes variants of Annexin A5 with the extension of N-terminus part of Annexin A5 with an extra set of amino acids of which one is a cysteine residue. The extra amino acids with the cysteine residue are introduced with the purpose to chelate spontaneously the $^{99m}Tc$ radionuclide thereby obliterating the need for conjugation chemistry in order to radiolabel Annexin A5. This is only possible for compounds that show spontaneous and non-covalent attachment to the sulfhydryl groups. The problem with this type of interaction is the ability of the chelate reaction to reverse, i.e., the attached compound can dissociate from the Annexin A5 variant. The rate of dissociation depends on several factors, such as the compound and the amino acids capturing the compound.

SUMMARY OF THE INVENTION

In accordance with one embodiment of the invention there is provided a new and improved complex that has at least one pharmaceutical compound and an annexin, where the annexin binds to at least one aminophospholipid and facilitates internalization of the pharmaceutical compound into a cell. Several annexins and derivatives thereof can be used in accordance with this invention. Additionally, a new and improved annexin variant can be used in the complex. Such an annexin variant is a protein that is folded to provide a configuration where the annexin has a convex side and a concave side. The convex side is used to bind with at least one phospholipid and the concave side is made of amino acids, where at least one amino acid on the concave side is a cysteine residue. In an alternate embodiment, the protein comprises a derivative of the annexin variant, where at least one other natural amino acid is substituted with a different amino acid and where the amino acid substitution does not substantially affect the ability of the variant to bind to at least one negatively charged phospholipid and to bind at least one pharmaceutical compound, carrier, or cross-linker. Another embodiment of this invention relates to a method of making the complex described above including coupling the annexin to at least one pharmaceutical compound or at least one carrier of at least one pharmaceutical compound, either directly or indirectly by a cross-linker.

Another embodiment of the invention is a device for detecting the presence or absence of cells or cell particles expressing phospholipids that includes a solid support and at least one annexin, where the annexin is covalently attached to the support, either directly or indirectly, and where the annexin captures cells and cell-derived particles expressing phospholipids on their surfaces from fluids of the subject. In addition, the invention includes, as another embodiment, a method for detecting the presence or absence of cells or cell particles expressing phospholipids that includes contacting fluids of the subject with the device described above and detecting the presence of the cells or cell particles associated with the device.

Another embodiment of the present invention is a kit that includes at least one complex described above and, optionally, at least one pharmaceutically acceptable excipient.

One embodiment of the present invention relates to a method for delivering a pharmaceutical compound to a target cell that includes administering a therapeutic composition of the complex that is described above. More specifically this embodiment encompasses a method to treat or prevent a disease, where the pharmaceutical compound is a therapeutic compound that is effective to treat or prevent the disease.

Another embodiment of the invention relates to the method for delivering a pharmaceutical compound to a target cell that is used to detect the presence or absence of cells or cell particles expressing phospholipids. Additionally, the method for delivering a pharmaceutical compound to a target cell can be used for prevention of a disease and for research of a disease.

For a better understanding of the present invention, together with other and further objects thereof, reference is made to the following description, taken in conjunction with the accompanying drawings, and its scope will be pointed out in the appending claims.

BRIEF DESCRIPTION OF THE DRAWINGS

FIG. 1 illustrates SEQ ID NO: 1. This sequence is the amino acid sequence of human Annexin A5. The amino acids are given in the one-letter code. The underlined amino acids form the concave surface of the Annexin A5 molecule as based upon the 3D-structure elucidated by Huber, et al., EMBO J 9:3867-74 (1990a). Embodiments of this invention include proteins with this sequence having one of the underlined amino acids replaced by a cysteine residue.

FIG. 2 is an embodiment of the invention and illustrates SEQ ID NO: 2. This sequence is the amino acid sequence of the Annexin A5 variant. The amino acids are given in the one-letter code. This sequence differs from the human Annexin A5 sequence (Maurer-Fogy, et al., Eur. J Biochem. 174:585-92 (1988)) at position 315, which contains here a Serine residue (indicated in bold). The human Annexin A5 sequence contains a Cysteine residue at position 315. The underlined amino acids form the concave surface of the Annexin A5 molecule as based upon the 3D-structure elucidated by Huber, et al., EMBO J 9:3867-74 (1990a). Embodiments of this invention include proteins with this sequence having one of the underlined amino acids replaced by a cysteine residue.

FIGS. 3a, b, c, and d are embodiments of the invention and illustrate SEQ ID NOS: 3, 4, 5, and 6. These sequence are examples of the annexin variants within the scope of this invention. Amino acids at positions 5, 7, 9, and 11, respectively, were replaced with cysteine residues (indicated in bold).

FIG. 4 is an embodiment of the invention and illustrates SEQ ID NO: 7. This sequence is an example of one of the annexin variants within the scope of this invention as described in Example 3.

FIG. 5A is an embodiment of the invention and illustrates the cell population distribution of the Jurkats prior to the treatment with the Annexin A5-Cys2-beads.

FIG. 5B is an embodiment of the invention and illustrates the cell population distribution after depletion of the phosphatidylserine exposing cells and particles by the treatment with beads.

FIG. 5C is an embodiment of the invention and represents the cells and particles that bound to the Annexin A5-Cys2- beads and are released by ethylene diamine tetra acetate ("EDTA") or dithiothreitol ("DTT").

DETAILED DESCRIPTION OF THE PREFERRED EMBODIMENTS

Before describing the present invention in detail, it must be understood that this invention is not limited to particularly exemplified compositions, formulations, or process parameters as such may vary. It is also to be understood that the terminology used herein is for the purpose of describing particular embodiments of the invention only and is not intended to be limiting. Further, it must be noted that, as used in the specification and the appended claims, the singular forms "a," "an," and "the" include plural references unless the content clearly states otherwise. Thus, for example, reference to "a particle" includes a mixture of two or more such particles, reference to "a pharmaceutical" includes mixtures of two or more such agents, and the like.

The present invention provides methods and compositions for the treatment, diagnosis, prevention, and research of diseases, such as neoplastic diseases, neurodegenerative diseases, cardiovascular diseases, autoimmune diseases, and inflammatory diseases. The methods include the administration to subjects of pharmaceutical complexes comprising annexins and annexin variants coupled to pharmaceutical compounds or carriers. The present invention also provides methods and compositions for delivering pharmaceutical compounds into target cells of a subject to, for example, kill them, such as tumor cells, or to rescue them, such as cardiomyocytes and neurons.

Cells are enveloped by a plasma membrane ("PM") that consists of a bilayer of phospholipid molecules and several protein molecules. Various phospholipid molecules form the building blocks of the bilayer. The molecules are asymmetrically distributed over the two layers, or leaflets, of the PM. Phosphatidylcholine for example is present in both layers, whereas sphingomyeline can be found only in the outer leaflet facing the environment. Aminophospholipids, like phosphatidylserine ("PtdSer"), on the other hand, are predominantly present in the inner leaflet facing the cell's cytosol (Zwaal, et al., Blood 89:1121-32 (1997)). Aminophospholipid translocases transport PtdSer from the outer to the inner layer, or leaflet, of the plasma membrane to create an asymmetric distribution of PtdSer (Diaz, et al., J. Membr. Biol. 151:1-9 (1996)). The asymmetric architecture of the PM is a feature of living cells. They expend energy to generate and maintain the uneven distribution of the phospholipid species in their PMs.

A cell can change the phospholipid architecture of its PM under certain circumstances, which lead to activation and perturbation of the cell. Programmed cell death ("PCD") is associated with the appearance of PtdSer in the outer leaflet of the PM (Fadok, et al., J. Immunol. 148:2207-16 (1992)). On the basis of morphology and biochemistry, four types of PCD have been identified: (1) apoptosis, (2) apoptosis-like PCD, (3) Necrosis-like PCD, and (4) necrosis (Leist, et al., Nat. Rev. Mol. Cell Biol. 2:589-98 (2001)). Each type is accompanied by a change in the asymmetry of the PM characterized by exposure of PtdSer to the outer layer of the cell surface. PtdSer exposure at the outer layer of the PM is a good indication of a variety of activated and perturbed states of a cell. PtdSer exposure, however, is not exclusively associated with cellular processes culminating in cell death. Transient and reversible PtdSer exposure has been reported for several cell types, including activated B-cells (Hammill, et al., Experimental Cell Research 251:16-21 (1999)), undifferentiated muscle cells prone to form syncytium (Van den Eijnde, et al., J. Cell Sci. 114:3631-42 (2001)), chlamydia infected cells (Goth, et al., Infect Immun. 69:1109-19 (2001)), endothelial cells of tumor vasculature (U.S. Pat. No. 6,312,694), and engulfing macrophages (Hamon, et al., Nat Cell Biol 2:399-406 (2000)). In addition, several cellular processes and conditions have been found that are associated with an expression of PtdSer at the outer leaflet of the plasma membrane. These include platelet activation (Bevers, et al., Eur. J. Biochem. 122:429-36 (1982)), red blood cell ageing (Schroit, et al., J. Biol. Chem. 260:5131-38 (1985)), stimulation of the immune system (Martin, et al., Intern. Arch. Aller. Immunol. 123:249-58 (2000); Hammill, et al., Exp. Cell. Res. 251:16-21 (1999)) muscle cell syncytium formation (Van den Eijnde, et al., Eur. J. Cell Biol. 114:3631-42 (2001)), new blood vessel formation in tumors (Ran, et al., Cancer Res. 62(21):6132-40 (2002)), and tumor growth (Rao, et al., Thromb. Res. 67:517-31 (1992)).

In addition, cells can dissipate portions of themselves from their surfaces resulting in membrane encapsulated microparticles. These microparticles have aminophospholipids exposed at the outer layer of the membranes' surfaces (Dachary-Prigeflt, et al., 22:157-164 (1996), Casciola-Rosen, et al., Proc. Natl. Acad. Sd. U.S.A. 93:1624-29 (1996)). These microparticles have been associated with diseases like infection (Satta, et al., Journal of Immunology 153:3245-55 (1994)), AIDS (Aupeix, et al., J Clin Invest. 99(7):1546-54 (1997)), atherosclerosis (Mallat, et al., Circulation 99:348-53 (1999)), and acute coronary syndromes (Mallat, et al., Circulation 101:841-843 (2000)). Therefore, aminophospholipids at the cell surface are indicators of a variety of activated and perturbed states of a cell. Moreover, microparticles that exhibit exposed aminophospholipids reflect distant cell activation and perturbation. Hence, phospholipids at the surface of a PM constitute attractive targets for a variety of purposes including research, diagnosis, prevention, and treatment of diseases, as well as isolation and removal of aminophospholipid containing microparticles and cells. Preferably, PtdSer in the outer layer of a PM constitutes a target for research, diagnosis, prevention, and treatment of diseases.

The present invention relates to the ability of annexins to bind to PtdSer expressing cells and to induce the internalization of membrane patches that express PtdSer. This internalization results in the formation of intracellular vesicles containing the annexin. Annexins are able to induce internalization in vitro and in vivo. The internalization process differs from the recently discovered pinocytic pathways (Conner, et al., Nature 422:37-44 (2003)) and results when an annexin crystallizes on the phospholipid membrane (Oling, et al., J. Mol. Biol. 304:561-73 (2001)). Crystallization at the membrane surface is a shared feature of annexins (Gerke, et al., Physiol. Rev. 82:331-71 (2002)). The present invention relates to the use of annexins to open these novel portals of entry to shuttle therapeutic compounds into a cell. The present invention provides methods for delivering a pharmacological compound to a target cell and complexes comprising an annexin and one or more pharmacological compounds, such as diagnostic, preventative, and therapeutic compounds and such as polymers of nucleic acids, small chemical entities, peptides, polypeptides and proteins that should act inside the diseased cells either to kill them or to rescue them.

Annexins constitute a multigene family of proteins that share structural and functional features. The annexin polypeptide is organized in domains that form the so-called Annexin fold in space (Gerke, et al., Physiol. Rev. 82:331-71 (2002)). The domains contain calcium binding sites through which an interaction with phospholipid membranes can occur. Once bound to a phospholipid's surface the annexins can form a two-dimensional lattice through protein-protein interactions. (Oling, et al., J. Mol. Biol. 304:561-73 (2001)). The physiological significance of the annexins is poorly understood but is thought to be related to their phospholipid binding activity. The annexins do not have a signal sequence and therefore are thought to play a role within the cell. Extracellular localization of annexins have been reported but it is unknown whether this has happened by a selective process or by an specific event such as cell lysis.

In a preferred embodiment, the annexin is Annexin A5, a derivative of Annexin A5, Annexin A8, a derivative of Annexin A8, or a combination thereof. Annexin A5 is a protein that binds to phospholipids, such as PtdSer, (Van Heerde, et al., Thromb. Haemost. 73:172-179 (1995), Seaton, et al., Biometals 11:399-404 (1998)). Once expressed at the surface of the cell, PtdSer acts as a receptor to Annexin A5, which binds with high affinity and in a calcium-dependent manner to this phospholipid species (Tait, et al., J. Biol. Chem. 264: 7944-49 (1989); Andree, et al., J. Biol. Chem. 265:4923-28 (1990)). This property has been exploited by using Annexin A5 as a tool to measure PCD in vitro (Van Engeland, et al., Cytometry 31(1):1-9 (1998); U.S. Pat. No. 5,834,196; Martin, et al., J. Exp. Med. 182:1545-56 (1995); Koopman, et al., Blood, 84:1415-20 (1994); Homburg, et al., Blood 85:532-40 (1995); Vermes, et al., J. Immunol. Methods 184:39-51 (1995)), in vivo in animals (Van den Eijnde, et al., Cell Death Differentiation 4:311-316 (1997); Dumont, et al., Nat Med 7:1352-5 (2000); Blankenberg, et al., Proc. Natl. Acad. Sd. 95:6349-54 (1998); U.S. patent application Ser. No. 2002/0192162), and in humans (Hofstra, et al., Lancet 356:209-212 (2000); Hofstra, et al., Jama 285:1841-2 (2001), Narula, et al., Nat. Med. 7:1347-52 (2001); U.S. Pat. No. 6,197,278). Annexin A5 has also been used to measure and capture microparticles (Mallat, et al., Circulation 99:348-53 (1999); (Mallat, et al., Circulation 101:841-843 (2000); Nieuwland, et al., Circulation 96:3534-3541 (1997)). The phospholipid binding ability of Annexin A5 has been elaborated as a targeting function to direct bioactive compounds such as urokinase to phospholipid exposing cells (Tait, et al., Journal of Biological Chemistry 270:21594-99 (1995)).

Annexin A8 is also a protein that binds to phospholipids and it can similarly be employed according to the present invention. For example, Annexin A8 can be coupled with a pharmaceutical compound and employed to facilitate internalization of the compound. Annexin A8's sequence is well-known in the art was published by Hauptmann, et al. in Eur. J. Biochem. 185:63-71 (1989).

The present invention takes advantage of the properties of annexins and is based, at least in part, on the discovery that Annexin A5 binds to PtdSer expressing cells and induces internalization and intracellular vesicle formation of the PtdSer expressing membrane patches. A preferred embodiment relates to a complex that has at least one pharmaceutical compound and an annexin, where the annexin binds to at least one phospholipid and facilitates internalization of the pharmaceutical compound into a cell. The annexin is preferably folded to provide a configuration with a convex side that can bind with at least one phospholipid and a concave side comprising amino acids, wherein at least one amino acid on the concave side is a cysteine residue. In addition, the convex side preferably does not contain a cysteine residue.

The present invention is also based, in part, on observations that the intracellular vesicles contain the Annexin A5, which causes the internalization of the membrane patches. The internalization of Annexin A5 occurs not only in vitro by apoptotic and viable cells with reversible PtdSer expression but also in vivo, as evidenced by a mouse model of ischemia/reperfusion injury of the heart that shows PtdSer expressing cardiomyocytes in the area at risk internalize fluorescent Annexin A5, that was administered into the blood circulation. See Examples 1 and 2. Additionally, a mouse model of tumor growth shows that tumor cells internalize fluorescent Annexin A5, that was administered to the blood circulation. The amount of internalized fluorescent Annexin A5 by the tumor increased from treating the tumor with cytotoxic drugs.

Annexin A5 also shuttles compounds that are coupled to fluorochromes. Fluorochromes can be replaced by therapeutic compounds or carriers containing therapeutic compounds. See Example 3. The examples demonstrate that Annexin A5 couples to phospholipid coated paramagnetic particles of 1-10 µm in diameter and shuttles these particles into the cell. From these findings, one of skill in the art would understand that Annexin A5 is able to induce internalization of compounds varying in size from about 100 Da in molecular weight to macromolecular structures of about 10 µm in size. It is possible that even larger molecules may be internalized. Accordingly, the present invention preferably embodies compositions of Annexin A5 and therapeutic compounds or carriers containing therapeutic compounds that are covalently linked to Annexin A5. The intracellular vesicle formation caused by Annexin A5 is driven by cellular mechanisms that are different from the ones responsible for the known pinocytic pathways, such as fluid phase internalization, receptor-ligand mediated internalization, and caveolae associated internalization (Conner, et al., Nature, 422:37-44 (2003)).

Annexin A5 opens this novel portal into the cell by its ability to form a two-dimensional lattice on the phospholipid surface. The Annexin A5 variant, M23, which binds to PtdSer, lacks the ability to form a two-dimensional lattice on the phospholipids surface and therefore does not open this novel portal of entry and remains at the outside of the cell in vitro and in vivo. Example 2 provides evidence of this by infusing fluorescently labeled M23 into a mouse, which suffered from ischemia/reperfusion injury of the heart. Unlike fluorescently labeled Annexin A5, the M23 variant is not internalized by the cardiomyocytes in the area at risk but remains attached to the sarcolemmal surface of the cells.

In a preferred embodiment, the annexin used in the complex is an annexin variant. Annexin variants are related to natural annexins, such as Annexin A5, and their derivatives, such as Annexin A5/Ser315, but they are engineered to have one or more cysteine residues at defined and predetermined sites on the annexin molecule. The cysteine residue enables the annexin to chemically link with another compound, for example, a pharmaceutical compound, generating a complex. In a preferred embodiment, the interaction yields a one to one stoichiometric complex. Specifically, in a preferred embodiment, the annexin molecule has one cysteine residue engineered and exposed that can chemically link to another compound, resulting in a complex. It is also preferable that the cysteine residue is engineered in a specific location, so that the compound will not interfere with the annexin's other binding properties. As such, the complex retains the phospholipid binding property of the annexin and, more specifically, the annexin's biological activity of binding to membranes containing phospholipids. See Examples 4-9. In addition, it retains the ability to facilitate internalization of a compound as described.

The polypeptide chain of human Annexin A5, for example, contains a tandem of four homologous domains (Maurer-Fogy, et al., Eur. J Biochem. 174:585-92 (1988)), each bearing an endonexin fold (Geisow, et al., Nature 320:636-8

(1986)). This endonexin fold motif mediates the binding of the annexin to the phospholipids (Huber, et al., FEBS Lett 275:15-21 (1990b)). The three dimensional structure of the annexin facilitates the organization of the polypeptide chain. The domains fold as distinct modules thereby orienting the phospholipid binding sites at one side of the molecule (Huber, et al., EMBO J 9:3867-74 (1990a)). This side has a convex shape. The opposite side has a concave curvature and harbors the first 19 residues of the N-terminal tail of Annexin A5. When Annexin A5 is bound to the phospholipids its concave surface points away from the phospholipid surface into the solution (Oling, et al., J Struct. Bid 133:55-63 (2001)). SEQ ID NO: 1 is the amino acid sequence of human Annexin A5 and SEQ ID NO: 2 is the amino acid sequence of its variant, Annexin A5/Ser315.

The amino acids at the concave surface of Annexin A5 and Annexin A5/Ser315, are underlined in the sequences illustrated in FIG. 1 and FIG. 2, and include amino acid positions 1-19, 24, 28, 46-64, 86-89, 118-135, 150, 157-170, 202-219, 245-248, and 280-294. Derivatives of these variants are also contemplated. Annexin A5/Ser315 is an engineered derivative in which Cys315 is replaced by Ser315 and is particularly important because of its ability to avoid possible intramolecular disulfide bridge formation when a cysteine is engineered at positions at the concave side of the molecule. Cys315 is not on the concave side of the correctly folded molecule, however, during translation it may form an intramolecular disulfide bridge with cysteine at upstream positions thereby annihilating the possibility to chemically link a compound to the upstream cysteine and thereby potentially destroying the biologically active conformation. The variants and derivatives preferably maintain the annexins' ability to bind with at least one phospholipid and to facilitate internalization of a compound as described.

The invention is based, in part, on the elucidation of the tertiary structures of the annexins and the findings that annexins bind with their convex surface to the phospholipid membrane and point their concave surface away from the surface into the solution. The embodiments of this invention include annexin variants, which have at least one cysteine residue located at the concave surface of the molecule. This preferably occurs by the substitution of a natural amino acid with a cysteine residue or alternatively, the sequence can be engineered by recombinant methods. Those skilled in the art will know of alternate methods of making these variants and derivatives. In a preferred embodiment, the convex side does not contain a cysteine residue. In a further preferred embodiment, the cysteine residue on the concave side does not interfere with the annexin variant's ability to bind with at least one phospholipid and to facilitate internalization of a pharmaceutical agent.

Amino acid positions 1-19, 24, 28, 46-64, 86-89, 118-135, 150, 157-170, 202-219, 245-248, and 280-294 are specifically identified because of their orientation. These sites are particularly desirable because they are directed away from the phospholipid binding sites on the convex side of the annexin molecule that will interact with the phospholipids in the outer layer of a cell's PM. One or more of these amino acids may be replaced for a cysteine residue. Methods for production of the modified amino acids include eukaryotic hosts such as insect cells and yeast. These expression systems require eukaryotic expression vectors. The sequence of the Annexin A5 variants are not changed for eukaryotic expression. One of skill in the art will recognize that replacement of an amino acid may occur by way of substitution or the amino acid sequence may be engineered or created to include the cysteine residue. The cysteine residue can interact with a compound to form a complex. A complex in this orientation will bind to membranes containing phospholipids and facilitate internalization of the pharmaceutical compound into a cell. The internalization can occur in vitro or in vivo.

In a preferred embodiment of the invention, the annexin variant can bind to a phospholipid, and preferably a negatively charged phospholipid or aminophospholipid, with a dissociation constant of approximately $10^{-6}$ M or less in the presence of $Ca^{2+}$ ions. The phospholipids in accordance with this invention are preferably connected to a membrane and can be selected from phosphatidylserine, cardiolipin, and phosphatidic acid, for example. The membrane can be from a number of sources, including cell membranes and membrane encapsulated microparticles. A cell is, for example, a cell culture, a tissue cell, an organ cell, an organism, an animal cell, a mammalian cell, and a human cell. A subject is, for example, an organism, an animal, a mammal, or a human.

In an alternate embodiment, the protein comprises a derivative of the annexin variant, where at least one other natural amino acid is substituted with a different amino acid and where the amino acid substitution does not substantially affect the ability of the variant to bind to at least one negatively charged phospholipid, to facilitate internalization of the pharmaceutical compound into a cell, and to bind at least one pharmaceutical compound, carrier, or cross-linker.

As discussed, the annexin variant described herein can be used according to the complexes, methods, kits, and devices that are also described herein. For example, the annexin variant can be used to form a complex as described above for Annexin A5 that is made of at least one pharmaceutical compound and an annexin variant, where the annexin variant binds to at least one negatively charged phospholipid and facilitates internalization of the pharmaceutical compound into a cell, and where the pharmaceutical compound is chemically linked either directly or indirectly via a carrier, a cross-linker, or both a carrier and a cross-linker to at least one cysteine residue in the annexin variant or variant thereof. The annexin variant has the properties described above, and the complex has many of the same properties as the complex described above and can use the same pharmaceutical compounds, carriers, linkers, etc.

The compound that links to the annexins or variants thereof can be therapeutic compounds, diagnostic compounds, preventative compounds, or research compounds, as described below. One of skill in the art will recognize that there are many compounds that are useful in the claimed invention beyond therapeutic compounds, diagnostic compounds, research compounds, preventative compounds, and research compounds. The list described below is therefore exemplary and the compounds listed in this specification are preferred embodiments.

In a preferred embodiment, the pharmaceutical compound in the complex is covalently complexed either directly or indirectly via a carrier, a cross-linker, or both a carrier and a cross-linker to the annexin. Annexin can bind to more than one pharmaceutical compound. For example, one compound can couple to an amino group of annexin and the other compound can couple to a sulfhydryl group of the annexin. Alternatively, a liposome carrier containing a mixture of pharmaceutical compounds can couple to an amino group or a sulfhydryl group of the annexin.

The term "pharmaceutical compound" is generally used to refer to a compound that has biological activity. In a preferred embodiment, the pharmaceutical compound is selected from the group consisting of a therapeutic compound, a diagnostic compound, a preventative compound, and a combination thereof.

Therapeutic compounds are, for example, a toxin, an enzyme, a lipid, a carbohydrate, an immunoglobulin or a fragment thereof, an immunoconjugate, a chemotherapeutic compound, a photosensitizer, a radionuclide, a cell death inducing agent, a cell death inhibiting agent, a fibrinolytic compound, and a combination thereof. Exemplary toxins are Dt, PE, P38, P40, ricin, abrin, diphtheria toxin, cholera toxin, gelonin, pseudomonas exotoxin, shigella toxin, and pokeweed antiviral protein. Exemplary enzymes are peroxidases, alkalases, and caspases.

Lipids are, for example, phospholipids, fatty acids, prenelenes, and steroids. A lipid can be embedded in the membrane of a liposome. Exemplary chemotherapeutic compounds are BiCNU, bleomycin, busulfan, CCNU, carboplatin, carboplatinum, carmustine, cisplatin, cisplatinum, chlorambucil, 2-cholrodcoxyadenosine, cladribine, cytarabinc, cyclophosphamide, dacarbazine, daunorubicin, docetaxel, doxorubicin, DTIC, etoposide, 5-flourouracil, fludarabine, gemcitabine, hydroxyurea, idarubicin, ifosfamide, irinotecan, lomustine, melphelan, methotrexate, mithramycin, mitomycin, mitoxantrone, nitrogen mustard, oxaliplatin, paclitaxel, plicamycin, procarbazine, raltitrexed, semustine, tomudex, topotecan, vinblastine, vincristine, and vinorelbine. Therapeutic radionuclides are, for example, Iodine-131, Rhenium-186, Strontium-89, and Yttrium-90. Photosensitizers are, for example, phtalocyanines, rhodoporphyrins, rhodochlorins, mesorhodochlorins, phyllocrythrin and its derivatives, porphorin and its derivatives, and metal-pyrollic compounds.

Examples of cell death inducing agent are apoptosis inducers, kinase inhibitors, activators of mitochondrial permeability transition, polynucleotides encoding for a cell death inducing protein, activators of ion-transport across the membrane, polynucleotides being an anti-sense to polynucleotides encoding for cell death inhibiting proteins, and polynucleotides interacting with and inhibiting cell death inhibiting proteins. Cell death inhibiting agents are, for example, apoptosis inhibitors, caspase inhibitors, cathepsin inhibitors, inhibitors of ion-transport across the membrane, inhibitors of mitochondrial permeability transition, growth factors, polynucleotides encoding for cell death inhibiting proteins, polynucleotides being an anti-sense to polynucleotides encoding for call death inducing proteins, and polynucleotides interacting with and inhibiting cell death inducing proteins.

Diagnostic compounds are, for example, a fluorescent group, a contrast agent, a photosensitizer, a radionuclide, an ultrasound agent, and a combination thereof. Exemplary fluorescent groups are Fluorescein-isothiocyanate ("FITC"), oregon green, alexa, phycoerythrine, cy-compounds, propidium iodide, 7-AAD, sytox-compounds, and nanocrystals, such as Cadmium-Selenide, Lead-Selenide, Indium-Phosphide, and Gallium-Arsenide. Contrast agents are, for example, gadolinium, magnetic particles, paramagnetic particles, and air bubbles. Photosensitizer are phtalocyanines, rhodoporphyrins, rhodochlorins, mesorhodochlorins, phyllocrythrin and its derivatives, porphorin and its derivatives, and metal-pyrollic compounds. Diagnostic radionuclides are, for example, Carbon-11, Fluorine-18, Indium-111, Iodine 123, Iodine-131, Nitrogen-13, Oxygen-15, Technetium-99m, Zirconium-89, and a combination thereof.

The pharmaceutical compounds described above are exemplary. Those skilled in the art will know of other compounds that can be used in accordance with the invention disclosed in this specification.

In a preferred embodiment, the annexins described herein can be coupled with cross-linkers as indicated above to carriers containing pharmaceutical compounds such as liposomes or dendrimers. A cross-linker according to the present invention covalently bonds a pharmaceutical compound or a carrier of at least one pharmaceutical compound with at least one amino acid of the annexin, with at least one primary amino group, or with at least one sulfhydryl group of an amino acid of the annexin. In a preferred embodiment, the cross-linker reacts with a group other than an amino group of the pharmaceutical compound or the carrier. The cross-linker can be N-succinimidyl 3-(2-pyridyldithio)propionate, N-succinimidyl maeimidoacetate, N-succinimidyl 3-maleimidoproprionate, N-succinimidyl 4-(N-maleimidomethyl)cyclohexane-1-carboxylate, pyridyl, maleimide containing groups, halogen containing groups, an isothiocyanate, an isocyanate, an imidoester, and a succinimidylester group.

A carrier in accordance with this invention is, for example, a liposome, a dendrimer, a polymer, or a combination thereof. Preferably, the carrier is a polymer that can encapsulate pharmaceutical compounds. Liposomes may be composed of bilayers of lipids encapsulating the pharmaceutical compounds. All or part of the lipids may comprise of phospholipids. All or part of the lipids or polymers may provide the chemical group to react with one or more of the reactive groups of the cross-linker or annexin to form a chemical link with the pharmaceutical compound. The chemical group can be an amino group, a sulfhydryl group, or a hydroxyl group. The lipid carrier can be stabilized by compounds such as cholesterol and polyethylene glycols. The lipid carrier can vary in size from 20 nm to 10 μm in diameter. The lipid carrier can be uni- or multi-lamellar of structure. An example of a liposome carrier is a 100 nm liposome consisting of phospahtidylcholine/phosphatidylethanomine/cholesterol in a molar ratio of 46/20/34 carrying the cytostatic agent doxorubicin. Appropriate amounts of the indicated lipids in chloroform are mixed in a glass tube. The solvent is evaporated leaving the lipids in a dry film on the glass wall. A buffered solution of pH>7.5 containing 50 mg/ml doxorubicin is added and the lipids are suspended by vigorous mixing. The lipid suspension is extruded through a filter containing pores of 100 nm in diameter. The extruded liposomes have a size around 100 nm in diameter and contain doxorubicin. 1-10 mM SPDP is added to the extruded liposomes. This results in a reaction between the succinimidylester of SPDP and the amino group of phosphatidylethanolamine. The reaction product is dialyzed into a buffer of pH<7.5 and subsequently mixed with an Annexin A5 variant containing a cysteine residue at its concave side such as Cys2-Annexin A5 or Cys7-Annexin A5. This results in a reaction between the pyridyl moiety of the PDP group attached to the liposome and the sulfhydryl group of the Annexin A5. The result is a covalent complex between Annexin A5 and the doxorubicin containing liposome in which Annexin A5 has retained full negatively charged phospholipid binding activity. Those of skill in the art will know of other cross-linkers and carriers that can be easily utilized according to the present invention.

Excipients in accordance with this invention are, for example, water, cations, anions, stabilizing proteins, stabilizing carbohydrates, and chelating agents. Those skilled in the art will know of other excipients which can be incorporated into a pharmaceutical composition, but which do not adversely affect the activity of the active ingredient.

Diseases in accordance with this invention are, for example, characterized by the expression of phospholipids in the outer layer of a plasma membrane in said subject. Diseases that can be treated and diagnosed are, for example, neoplastic diseases, cardiovascular diseases, infectious diseases, autoimmune diseases, neurodegenerative diseases, and a combination thereof. Specific diseases include ophtalmic disease, gastro/intestinal tract disease, and rheumatoid arthritis.

In another embodiment, the complex utilizes a derivative of annexin, for example, a derivative of Annexin A5. Annexin derivatives have one or more amino acid substitutions, deletions, additions, but the amino acid substitutions, deletions, or additions do not substantially affect the ability of the annexin to bind to at least one phospholipid, to facilitate internalization of the pharmaceutical compound into a cell, and to bind at least one pharmaceutical compound, carrier, or cross-linker. The nature of the derivatives in accordance with the invention consists of additions of amino acids at the N-terminus and C-terminus and substitutions of amino acids outside the phospholipids binding regions, e.g., at the concave side of the molecule. One derivative that is both exemplary and of particular importance is an Annexin A5 where Ser315 is substituted for Cys315. This derivative is identified as "Annexin A5/Ser315." Those with skill in the art know how to make such derivatives. Moreover, the examples describe how to test annexins and derivatives for their ability to bind to phospholipids, pharmaceutical compounds, carriers, and cross-linkers and to facilitate internalization of a pharmaceutical compound into a cell. See, e.g., Example 1.

Another embodiment of the present invention relates to a method for delivering a pharmaceutical compound to a target cell. The method includes administering a composition of the complex of the annexin or annexin variant and pharmaceutical compound, where the annexin or annexin variant binds to at least one phospholipid and facilitates internalization of the pharmaceutical compound into the target cell and where the pharmaceutical compound is chemically linked either directly or indirectly via a carrier, a cross-linker, or both a carrier and a cross-linker to the annexin or annexin variant, and, optionally, at least one pharmaceutically acceptable excipient. This method can be used to treat a disease, diagnose a disease, prevent a disease, or research a disease according to the embodiments described below.

Another embodiment of the present invention relates to a method for treating a subject in need of treatment of a disease that includes administering a therapeutic composition of the complex as described above, where the pharmaceutical compound is a therapeutic compound and, optionally, at least one pharmaceutically acceptable excipient. In a preferred embodiment, the methods employ annexin derivatives of this invention for delivering bioactive compounds to sites where cells and/or particles reside with exposed phospholipids. These sites can be in vitro as well as in vivo. The methods include administering to the subject a composition comprising a therapeutically effective amount of complex comprising at least one therapeutic compound and an annexin derivative.

Administration and dosage of a therapeutic drug can vary between patients and are well know in the medical art. The preferred dosage will depend upon the disease being treated, the therapeutic compound or mix of compounds, and the patient among other factors. Possible delivery routes of the complexes are subcutaneous, intra-muscular, intra-peritoneal and intravenous administration. Those of skill in the art would know of other delivery routes. Complexes can administered as a bolus or continuously per infusion covering a longer period of time. Doses range from 0.1 pg/kg to 10 mg/kg in diagnostic procedures and 1 pg/kg to 100 mg/kg in therapeutic procedures. Preferably 1 pg/kg-1 mg/kg (diagnostic) and 5 pg/kg-50 mg/kg (therapeutic). Those skilled in the art would know how to select the appropriate dosages for the specific subject and situation. The same principles must be considered when determining the dosage ranges of diagnostic and preventative compounds.

In a further embodiment of the invention, annexins can target bioactive compounds to the phospholipid exposing endothelial cells of tumor vasculature. Annexin variants of the present invention can be used to conjugate the bioactive compounds for the reasons disclosed in U.S. Pat. No. 6,312,694.

Another embodiment of the invention relates to a method for detecting the presence or absence of cells or cell particles expressing phospholipids that includes administering an effective composition comprising at least one complex as described above, where the pharmaceutical compound is a diagnostic compound and, optionally, at least one pharmaceutically acceptable excipient, and further detecting the presence of the diagnostic compound. The detecting step can be, but is not limited to, optical imaging, SPECT imaging, PET imaging, MRI imaging, CT imaging, and ultrasound imaging.

An embodiment of this invention relates to a method of making the complex described above including coupling the annexin or annexin variant to at least one pharmaceutical compound or at least one carrier of at least one pharmaceutical compound, either directly or indirectly by a cross-linker. For example, an annexin, such as Annexin A5, a variant, or derivative, is coupled to a pharmaceutical compound or a carrier of pharmaceutical compounds by a bifunctional cross-linker that covalently bonds with an amino acid of Annexin A5 on one side and with a reactive group on the pharmaceutical compound or carrier on the other side so as to link Annexin A5 with the pharmaceutical compound or carrier of pharmaceutical compounds covalently. The cross-linker can be selected from the group of cross-linkers that react with primary amino groups such as cross-linkers with an isothiocyanate, an isocyanate, an imidoester or a succinimidylester group. These groups can react with primary amino groups of amino acids of Annexin A5. Preferably the cross-linkers have hetero-functionality so as to react with a group other than an amino group of the pharmaceutical compound or carrier. Examples of such heterobifunctional cross-linkers are N-succinimidyl 3-(2-pyridyldithio)propionate ("SPDP"), N-succinimidyl maeimidoacetate ("AMAS"), N-succinimidyl 3-maleimidoproprionate ("BMPS"), and N-succinimidyl 4-(N-maleimidomethyl)cyclohexane-1-carboxylate ("SMCC").

As another example, an annexin, such as Annexin A5, a variant, or derivative, is coupled to a pharmaceutical compound or a carrier of pharmaceutical compounds by a bifunctional cross-linker that covalently bonds with a sulfhydryl group of an amino acid of Annexin A5 on one side and with a reactive group on the pharmaceutical compound or carrier on the other side so as to link Annexin A5 with the pharmaceutical compound or carrier of pharmaceutical compounds covalently. The sulfhydryl group can be introduced chemically by reacting Annexin A5 with compounds, such as SPDP, and subsequently with a reducing agent, such as DTT. The sulfhydryl group can also be introduced in Annexin A5 through molecular biology techniques yielding annexin variants with a single cysteine residue at the concave side of the molecule. The cross-linker can be selected from the group of cross-linkers that react with sulfhydryl groups such as cross-linkers with pyridyl, maleimide or halogen containing groups primary amino groups such as cross-linkers with an isothiocyanate, an isocyanate, an imidoester or a succinimidylester group. These groups can react with sulfhydryl groups of amino acids of Annexin A5. Preferably the cross-linkers have hetero-functionality so as to react with a group other than a sulfhydryl group of the pharmaceutical compound. Examples of such hetero-bifunctional cross-linkers are SPDP, AMAS, BMPS, and SMCC.

The bridge that joins the reactive groups of the cross-linker may embed various functionalities such as cleavable bonds. Cleavable bonds may be chosen such that separation between Annexin A5 and a pharmaceutical compound or a carrier of pharmaceutical compounds occurs preferably in predetermined tissues and cells. Cleavable bonds may be disulfide bonds or peptide sequences, which are cleaved by activated enzymes such as coagulation factors, fibrinolytic factors, caspases, cathepsins, metalloproteases, and elastases.

A further embodiment of the invention includes a device characterized by a solid support and annexin or variants thereof described herein attached to the support in order to capture and remove cells and cell-derived particles exposing phospholipids from fluids. Solid supports in accordance with this invention are, for example, metals, metal salts, magnetic materials, polymers of organic monomers, and polymers of carbohydrates. The device is used for detecting the presence or absence of cells or cell particles expressing phospholipids and it includes a solid support and at least one annexin or variants thereof, where the annexin is covalently attached to the support, either directly or indirectly, and wherein the annexin captures cells and cell-derived particles expressing phospholipids on their membrane surfaces from fluids of the subject. A subject is preferably an organism, an animal, a mammal, or a human.

In addition, the invention includes, as another embodiment, a method for detecting the presence or absence of cells or cell particles expressing phospholipids that includes contacting the cells of the subject with the device described above and detecting the presence of the cells of the subject associated with the device. The detecting step can be, but is not limited to, optical imaging, SPECT imaging, PET imaging, MRI imaging, CT imaging, and ultrasound imaging. In the context of this application, the terms "diagnosis" or "detection" can be used interchangeably, whereas diagnosis usually refers to defining a tissue's specific histological status, whereas detection usually refers to locating a tissue, lesion, or organism as either being present or absent. In addition, as described above, it is well known that the presence of cells or cell particles expressing phospholipids is indicative of a disease.

The embodiments of this invention include methods, which employ the annexin-solid support device for the measurement and/or isolation of phospholipid exposing cells and particles in and/or from a biological solution. WO 00/10673 is incorporated as a reference herein for the purpose of describing a device with Annexin A5 immobilized to a surface to capture phospholipid exposing cells and particles. Annexin A5, Annexin A8, variants, and derivatives of the present invention can be immobilized to a solid support to create such a device.

Another embodiment of the present invention is a kit that includes at least one complex described above and, optionally, at least one pharmaceutically acceptable excipient. The protein with the therapeutic, diagnostic, preventative, or research compound may be provided as a kit for human or mammalian use in a pharmaceutically acceptable injection vehicle, preferably phosphate-buffered saline ("PBS") at physiological pH and concentration. The preparation preferably will be sterile, especially if it is intended for use in humans. Optional components of such kits include stabilizers, buffers, labeling reagents, radionuclides, paramagnetic compounds, and conventional syringes, columns, vials and the like. Additionally, the kit can include containers and syringes or other delivery devices.

An embodiment of the invention includes methods for preventing the onset of a disease or impeding the progress of a disease in a subject at risk of the disease. In a preferred embodiment, the methods employ annexins or annexin variants of this invention for delivering bioactive compounds to sites where cells and/or particles reside with exposed phospholipids. These sites can be in vitro as well as in vivo. The methods include administering a composition comprising an effective amount of complex comprising at least one compound and an annexin or annexin variant.

An embodiment of the invention includes methods for researching a disease. In a preferred embodiment, the methods employ annexins or annexin variants of this invention for delivering research compounds to sites where cells and/or particles reside with exposed phospholipids. These sites can be in vitro as well as in vivo. The methods include administering a composition comprising an effective amount of complex comprising at least one compound and an annexin or annexin variant.

Alternative structures, functions, and operations are possible within the scope of the invention. Each publication, patent, and reference referred to in this specification is incorporated herein by reference in its entirety as if the reference had individually been incorporated by reference.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. All of the examples, methods and/or compositions disclosed, and claimed herein can be made and executed without undue experimentation in light of the present disclosure. While the methods and compositions of this invention have been described in terms of preferred embodiments, it will be apparent to those skilled in the art that variations may be applied to the methods and/or compositions and in the steps or in the sequence of steps of the methods described herein without departing from the concept, spirit and scope of the invention. It will be apparent to those skilled in the art that compositions with compounds which are structurally and functionally related may be substituted for compositions with the compounds described herein.

The following examples are merely intended to be exemplary and are not intended to limit the scope of the claims.

EXAMPLES

Example 1

Entry of Annexin A5-FITC and Annexin A5-Alexa568 into Cells in vitro and in vivo Annexin A5 can be purified from animal tissues as described by Funakoshi, et al., Biochemistry, 26:5572-78 (1987) or from bacteria, which are transformed with a cDNA encoding for Annexin A5, as described by Maurer-Fogy, et al., Eur. J. Biochem, 174:585-92 (1988). Fluorescent compounds can he coupled to amines of the Annexin A5 using procedures which are known to persons skilled in the art. In this example, we coupled FITC and Alexa568-succinimidy-lester to Annexin A5 to yield Annexin A5-FITC and Annexin A5-Alexa568, respectively.

Cultured Jurkat cells (ATCC) were activated to express PtdSer at their surface by stimulating them with anti-Fas antibody (clone 7C11, Beckman/Coulter, Mijdrecht, the Netherlands). This was done in the presence of 1-20 μg/ml fluorescently labeled Annexin A5. The Jurkat cells were analyzed for the localization of fluorescently labeled Annexin A5 by Confocal Scanning Laser Microscopy (CSLM, Bio Rad laboratories) after 1-3 hours of stimulation.

Fluorescently Annexin A5 was located in intracellular vesicles that were either attached at or detached from the plasma membrane. Intracellular localization was dependent on the presence of $Ca^{2+}$-ions and four functional $Ca^{2+}$/phospholipids binding domains of Annexin A5.

Hela cells (ATCC) were incubated with 1-20 μg/ml fluorescently-labeled Annexin A5 during 1-24 hours under non-perturbing conditions. The Hela cells were analyzed for the localization of fluorescently labeled Annexin A5 using CSLM. Fluorescently-labeled Annexin A5 was present in intracellular vesicles dispersed through the cytosol of the cell. The intracellular localization in Hela cells was also dependent on the presence of $Ca^{2+}$-ions and four functional $Ca^{2+}$/phospholipids binding domains of Annexin A5.

Ischemia/reperfusion injury was applied on the heart of a living mouse according to Dumont, et al., Nat. Med. 7:1352-55 (2001). Fluorescently-labeled Annexin A5 was injected into the tail vein during the reperfusion phase. At the end of the reperfusion period the heart was taken out, fixed, cut into sections and the sections were analyzed by CSLM. Cardiomyocytes in the area at risk had internalized fluorescently labeled Annexin A5 in intracellular vesicles dispersed through the cytosol. The internalization was dependent on the presence of four functional $Ca^{2+}$/phospholipids binding domains on the Annexin A5 molecule.

Tumor cells (Lewis lung carcinoma cells or Colon carcinoma cells) were injected into mice subcutaneously. When the subcutaneous tumors were larger than 5 mm in size fluorescently labeled Annexin A5 was injected into the tail vein of the mouse. Uptake of fluorescently labeled Annexin A5 by the tumor was imaged using the Optical Imaging device as described by Dumont, et al., Nat. Med. 7:1352-55 (2001). Tumors were then taken out, fixed, cut into sections and the sections were analyzed by CSLM. Fluorescently labeled Annexin A5 was present in intracellular vesicles in the cytosol of the tumor cells. Intracellular localization was dependent on the presence of four functional $Ca^{2+}$/phospholipids binding domains on the Annexin A5 molecule.

Example 2

Internalization of Annexin A5 is Driven by Two-Dimensional Lattice Formation and Accommodated by a Novel Portal of Entry Annexin A5 organizes on the phospholipids surfaces in arrays (two dimensional lattice) of trimers by protein-protein interactions (Oling, et al., J. Struct. Biol. 133:55-63 (2001)). Domains 2 and 3 are involved in the interactions within and between the trimers. In order to investigate the role of these domains we have inactivated the Ca2-/phospholipids binding function of these domains by site-directed mutagenesis of the Annexin A5 cDNA (domain 2: E228A, and domain 3: D303N according to Mira, et al., J. Biol Chem. 272(16):10474-82 (1997)). This variant, M23, was expressed in *E. Coli* and purified essentially according to the method described by Maurer-Fogy, et al., Eur. J. Biochem. 174:585-92 (1988).

Fluorescein-isothiocyanate or Alexa568-succinimidy-lester (Molecular Probes, Eugene) was coupled to the amines of M23 according to standard protocols known to persons skilled in the art.

Formation of two-dimensional lattices on the phospholipids surfaces was assessed FRET (fluorescence resonance energy transfer) analysis. Paramagnetic beads (1-4 μm in diameter) that were coated with a phospholipids bilayer containing PtdSer were incubated with mixtures of Annexin A5-FITC and Annexin A5-Alexa568 or mixtures of M23-FITC and M23-Alexa568. Fluorescence intensity of the beads was then measured by flow cytometry (Coulter Epics XL-MLC™) using an excitation of 488 nm and emission ranges of 515-530 nm (F11) and >600 nm (F13). The F11 and F13 profiles from different mixtures of FITC and Alexa568 labeled proteins showed that Annexin A5 binds to the beads and forms well-organized protein-protein interactions exhibiting FRET. M23 binds to the beads, however, without forming well-organized protein-protein interactions as displayed by the absence of FRET.

The in vitro and in vivo experiments as described under Example 1 were all carried out with M23-FITC and M23-Alexa568. The results of these experiments demonstrate that M23 binds to cells in vitro and in vivo without being internalized into intracellular vesicles, indicating that two-dimensional lattice formation of Annexin A5 on the cellular surface is required for internalization.

Hela-cells were further investigated on the mechanism through which Annexin A5 induces its internalization. Hela cells were incubated with 1-20 μg Annexin A5-Alexa568 and luciferin-yellow or transferring FITC or an inhibitor of caveolae to investigate fluid phase internalization, receptor-mediated internalization and caveolae-mediated internalization, respectively. Analyses of the Hela-cells with CSLM showed that Annexin A5 is internalized via a mechanism distinct from these well-known mechanisms, demonstrating a novel portal of cell entry opened by Annexin A5.

Example 3

Annexin A5 Transports Large Macromolecular Structures into the Cell

Annexin A5 induces internalization of compounds such as fluorescent compounds as was shown by Examples 1 and 2. In order to test whether Annexin A5 carries large macromolecular structures into the cell as well we constructed a variant of Annexin A5 having the Glutamine at position 2 replaced by a Cysteine and the Cysteine at position 315 by a Serine. This variant (Cys2-Annexin A5) was designed because it allows us to couple macromolecular structures to the Annexin A5 without impairing its ability to bind to PtdSer and to establish Annexin A5-Annexin A5 interactions on the cell surface. The N-terminal tail of Annexin A5 is apical to its phospholipids binding sites and does not interact with domains 2 and 3 (Huber, et al., EMBO J. 9:3867-74 (1990)).

This example describes the coupling of paramagnetic beads (1-4 μm in diameter) to Cys2-Annexin A5. Paramagnetic beads (PVE-12, Chemagen) were coated with phospholipids containing 1-20 mole % phoshatidylethanolamine ("PtdE"). The beads were activated with SPDP (Pierce Chemical Company) to yield activated PtdE, that reacts with sulfhydryl groups. Cys2-Annexin A5 was incubated with the SPDP activated beads according to standard protocols known to persons skilled in the art to yield phospholipid coated heads to which Cys2-Annexin A5 was covalently coupled (Cys2-

Annexin A5-beads). The Cys2-Annexin A5-beads contained Annexin A5 that was still able to bind to PtdSer and to PtdSer expressing cells.

Cys2-Annexin A5-beads were incubated with the lipophylic fluorescent probe CM-Dil (Molecular Probes, Eugene). Hela-cells were incubated with the stained Cys2-Annexin A-beads for 1-24 hours. Cells were then analyzed with CSLM. The results show that the covalently attached Cys2-Annexin A5 transports the large beads into the cells demonstrating that Annexin A5 is able to open the novel portal of entry for large macromolecular structures.

Example 4

Production of Annexin A5-Cys2 Variant having Amino Acid Glutamine at Position 2 Replaced by Amino Acid Cysteine The human Annexin A5 cDNA was prepared from a white blood cell cDNA library from a healthy volunteer with standard techniques known to persons skilled in the art. The cDNA sequence encoded the amino acid sequence presented in FIG. 1. Primers were designed to mutate Annexin A5 cDNA by PCR techniques such that the resulting cDNA encoded the amino acid sequence of FIG. 1 with the exception that the amino acid Glutamine at position 2 was replaced by the amino acid cysteine. The resulting cDNA encoded the Annexin A5-Cys2 variant.

The Annexin A5-Cys2 cDNA was cloned in the bacterial expression vector pCPSD with standard techniques known to persons skilled in the art. E.Coli were transformed with the resulting plasmid and grown in the Bioflo 3000 fermentor. The Annexin A5-Cys2 was isolated and purified from the E.Coli with standard techniques of ion-exchange and gel-permeation chromatography known to persons skilled in the art.

The purified Annexin A5-Cys2 showed a homogenous band of around 34 kDa on SDS-PAGE and exhibited full phosphatidylserine binding activity as measured by ellipsometry (Andree, et al., J Biol Chem 265:4923-4928 (1990)).

Example 5

The coupling of Annexin A5-Cys2 Variant to Magnetic Beads

This example represents a general and convenient coupling procedure in which an annexin variant of the embodiments of this invention is coupled to a (para)magnetic bead, which contains activated thiol groups. This example was carried out with uncoated M-450 Dynabeads from Dynal, Serum albumin from Sigma, the heterobifunctional and cleavable cross-linker SPDP from Pierce and recombinant Annexin A5-Cys2 variant.

Activation of the Magnetic Beads:

This example uses M-450 beads, Serum albumin to coat the beads and SPDP to activate the protein coat of the beads. M-450 beads may be replaced by any (para)magnetic beads. Serum albumin may be replaced by any protein or any carbohydrate compound. SPDP may be replaced by any cross-linking reagent thiolating the coat of the beads.

The beads are washed by placing a microfuge vial containing 1 ml of M-450 beads in the magnetic holder, aspirating the supernatant and resuspending the beads in 1 ml buffer (25 mM Hepes/NaOH, pH 7.4, 140 mM NaCl, and 1 mM EDTA). This wash procedure is repeated several times. Following the last wash the beads are resuspended in 1 ml buffer containing 100 mg/ml serum albumin. The vial is rotated head over end rotated preferably 120 minutes at ambient temperature. This generates an albumin coating on the beads. The beads are then washed several times with 1 ml buffer per wash to remove the unbound albumin. The albumin on the beads is thiolated by resuspending the beads in 1 ml buffer containing 150 µg/ml SPDP. This suspension is rotated head over end preferably 60 minutes at room temperature. Unreacted SPDP is then removed by washing the beads 4 times with 1 ml buffer per wash. The activation procedure yields magnetic beads with an albumin coat having exposed activated dithiogroups, which react spontaneously with proteins having sulfhydryl groups available on the surface of the protein to form a covalent bond between the protein and the albumin coat of the beads.

Covalent Bonding between the Activated Magnetic Beads and the Annexin Variant:

This examples describes the coupling of Annexin A5-Cys2 variant. Annexin A5-Cys2 variant may be replaced by any variant being part of the embodiments of this invention.

The activated magnetic beads (see section above) are collected using the magnetic holder. The solution is aspirated and the beads are resuspended in 1 ml buffer containing 5 mg Annexin A5-Cys2 variant. The reaction mixture is rotated head over end preferably 60 minutes at room temperature. The reaction is then stopped by washing the beads several times with 1 ml buffer per wash. The resulting beads have covalently attached Annexin A5-Cys2 variant, which is capable of binding to acidic phospholipids and cellular membranes, which have exposed acidic phospholipids like apoptotic cells, apoptotic bodies, and membrane derived microparticles.

Testing of Annexin A5-Cys2 Beads:

Jurkat cells ($10^6$ cells/ml culture medium) are triggered with 20 ng/ml anti-Fas antibodies to execute apoptosis for 4 hours at 37° C. 1 ml of activated Jurkat cells are then incubated with 50 µl of annexin V-Cys2-beads in the presence of 2.5 mM $Ca^{2+}$-ions in a microfuge tube during 15 minutes at room temperature. The tube is placed in the magnetic holder to separate beads and solution. The beads are washed thoroughly with binding buffer (25 mM Hepes/NaOH, pH 7.4, 140 mM NaCl, 2.5 mM $CaCl_2$). Finally the beads are resuspended in either EDTA buffer (25 mM Hepesf NaOH, pH 7.4, 140 mM NaCl, and 10 mM EDTA) or DTT buffer (25 mM Hepes/NaOH, pH 7.4, 140 mM NaCl, 2.5 mM $CaCl_2$, and 10 mM DTT). The beads are then removed from the solution. The solutions are mixed with Annexin V-FITC and Propidium Iodide and tested by flow cytometry.

FIG. 5A illustrates the cell population distribution of the Jurkats prior to the treatment with the Annexin A5-Cys2-beads. FIG. 5B illustrates the cell population distribution after depletion of the PtdSer exposing cells and particles by the treatment with beads. FIG. 5C represents the cells and particles that bound to the Annexin A5-Cys2-beads and are released by EDTA or DTT.

Example 6

The Coupling of Annexin A5-Cys2 Variant to the Fluorescent Protein Phycoerythrine This example represents a general and convenient coupling procedure in which an annexin variant of the embodiments of this invention is coupled to a protein with fluorescent properties. This example was carried out with phycoerythrine ("PE") from Molecular Probes, the heterobifunctional and cleavable cross-linker SPDP from Pierce and recombinant Annexin A5-Cys2 variant.

PE is dialyzed into a borate buffer at pH 8.5 and adjusted to 1 mg/ml. SPDP is dissolved in DMSO at a concentration of 6.2 mg/ml. 25 µl of the SPDP solution is added to 1 ml of the dialyzed PE. The reaction is allowed to proceed 30 minutes at room temperature. The reaction mixture is then dialyzed into sodium phosphate buffer at pH 7.2. Annexin A5-Cys2 is diluted into the PE solution at a concentration of 2 mg/ml. The mixture is allowed to react 60 minutes at room temperature. The Annexin A5-Cys2-PE conjugate is purified by gel filtration chromatography. The phosphatidylserine binding property of the Annexin A5-Cys2-PE conjugate is analyzed with ellipsometry. This analysis shows that the phosphatidylserine binding properties are not altered by cross-linking Annexin A5-Cys2 to a protein such as PE, which is about 6 times the size of Annexin A5-Cys2.

Example 7

The coupling of Annexin A5-Cys2 Variant to the phosphatidylethanolamine which is Embedded in the Membrane of a Liposome This example represents a general method to attach a phosphatidylserine targeting function to a drug delivery system of liposomes. This example illustrates moreover that structures, which are more than 100 times the size of Annexin A5-Cys2 can be coupled to Annexin A5-Cys2 via thiol chemistry without impairing its phosphatidylserine binding properties. This example was carried out with Dioleoyl-phosphatidylethanolamine ("PtdEth"), dioleoyl-phosphatidylcholine ("PtdChol"), and cholesterol ("Chol") from Avanti Polar Lipids, the heterobifunctional and cleavable cross-linker SPDP from Pierce and recombinant Annexin A5-Cys2 variant. A suspension of 5 mg/ml liposomes (PtdChol:PtdEth:Chol at molar ration of 8:10:1:1) is prepared in 0.1 M sodium phosphate buffer pH 7.5. Other lipids than PtdEth can be used if they contain a free amino-group in their hydrophilic headgroup. SPDP is dissolved at a concentration of 6.2 mg/ml in DMSO. Other heterobifunctional cross-linkers can be used if they contain reactive groups towards amino-groups and sulfhydryl moieties. 50 µl of the SPDP solution is added to 1 ml of the liposome suspension. The mixture is allowed to react 30 minutes at room temperature. The mixture is then dialyzed against 0.1 M sodium phosphate pH 7.2. Annexin A5-Cys2 is diluted into the liposome-suspension at a concentration of 2 mg/ml. The mixture is allowed to react 60 minutes at room temperature. The Annexin A5-Cys2-liposome conjugates are purified from the unreacted Annexin A5-Cys2 by centrifugation. The phosphatidylserine binding property of the Annexin A5-Cys2-liposome conjugate is analyzed with ellipsometry. This analysis shows that the phosphatidylserine binding properties are not altered by cross-linking Annexin A5-Cys2 to the large liposome structure.

Example 8

Targeting Doxorubicin Loaded Liposomes with Annexin A5-Cys2 Variant

This example represents a general method to attach an apoptotic cell targeting function to liposomes carrying cytostatics. The example was carried out with Distearoyl-phosphatidylchlorine, Cholesterol, and Distearoylphosphatidyl-ethanolamine-polyethylene glycol (2000)-maleimide ("PtdPE-PEGM"). The lipids were from Avanti Polar Lipids Inc. (USA, Alabaster Ala. 35007). Liposomes composed of PtdChol[PtdEPE-PEGM]/Chol in a ratio 50/20/30 (mole %) were prepared by hydration of a dry lipid film in 250 mM ammoniumsulfate pH 5.5. The multilamellar liposomes were extruded to a final size of around 100 nm. The external ammoniumsulfate was replaced with 10% sucrose by dialysis. The liposomes were loaded with Doxorubicin following a concentration driven mechanism as described in (Lasic, et al., Biochem. Biophys. Acta 1239:145-56 (1995)). The doxorubicin that was not taken up by the liposomes was removed by dialysis.

The doxorubicin loaded liposomes were dialyzed against Hepes buffer pH 7.2. Annexin A5-Cys2 was added and the mixture was incubated to allow a chemical reaction between the maleimide and the sulfhydryl group of Cys2. The resulting complex was analyzed for binding to a synthetic phospholipid surface containing phosphatidylserine and to apoptotic Jurkat cells.

Example 9

Annexin A5-Cys2 Targeted Doxorubicin Loaded Liposomes with a Imaging Function

This example represents a general method to attach an apoptotic cell targeting function to liposomes carrying cytostatics. In addition a diagnostic agent is covalent attach to the liposomes in order to track the trafficking of the liposomes in vivo by imaging techniques. The example was carried out with Distearoyl-phosphatidylcholine, Cholesterol, Distearoy 1 phosphatidyl-ethanolamine-polyethyle glycol (2000)-maleimide (PtdPE-PEGM) and Distearoylphosphatidyl-ethanolamine-polyethylene glycol (2000)-amine (PtdPE-PEGA). The lipids were from Avanti Polar Lipids Inc. (USA, Alabaster Ala. 35007). Liposomes composed of PtdChol/PtdEPE-PEGM/PtdEPE-PEGA/Chol in a ratio 40/20/10/30 (mole %) were prepared by hydration of a dry lipid film in 250 mM ammoniumsulfate pH 5.5. The multilamellar liposomes were extruded to a final size of around 100 nm. The external ammoniumsulfate was replaced with 10% sucrose by dialysis. The liposomes were loaded with Doxorubicin following a concentration driven mechanism as described in (Lasic, et al., Biochim Biophys Acta, 1239:145-56 (1995)). The doxorubicin that was not taken up by the liposomes was removed by dialysis. The doxorubicin loaded liposomes were dialyzed against Hepes buffer pH 7.4. The liposomes were mixed with diagnostic agents that react with the amine group. Examples are fluorescent probes with isothiocyanate groups or succinimidylgroups (for optical imaging), Gd-DTPA (for Magnetic resonance imaging), and radionuclear probes (for nuclear imaging). In this example, we used FITC. The doxorubicin loaded liposomes were mixed with FITC. The mixture was incubated to allow a reaction between the amine group and FITC. The uncoupled FITC was removed by dialysis. The doxorubicin loaded liposomes were dialyzed against Hepes buffer pH 7.2. Annexin A5-Cys2 was added and the mixture was incubated to allow a chemical reaction between the maleimide and the sulfhydryl group of Cys2. The resulting complex was analyzed for binding to a synthetic phospholipid surface containing phosphatidylserine using ellipsometry and to apoptotic Jurkat cells using flow cytometry.

Reference is made to a number of publications and patents in the present application in regard to their disclosures. There mentioned documents are herein incorporated in their entirety by reference.

What is claimed is:

1. A recombinant annexin variant comprising:
a convex side that can bind with at least one phospholipid; and
a concave side,
wherein an amino acid on the concave side selected from the group consisting of amino acids at positions 1-19, 24, 28, 46-64, 86-89, 118-135, 150, 157-170, 202-219, 245-248, and 280-294 of SEQ ID NO: 1 or SEQ ID NO: 2 has been replaced by a cysteine residue.

2. The annexin variant according to claim 1, wherein the convex side does not contain a cysteine residue.

3. The annexin variant according to claim 1, wherein the annexin variant binds to the phospholipid with a dissociation constant of approximately $10^{-6}$ M or less in the presence of $Ca^{2+}$ ions
wherein the phospholipid is selected from the group consisting of phosphatidylserine, cardiolipin, and phosphatidic acid.

4. A complex comprising:
at least one pharmaceutical compound; and
a recombinant annexin variant, wherein the annexin variant comprises a convex side that can bind with at least one phospholipid and a concave side,
wherein an amino acid on the concave side selected from the group consisting of amino acids at positions 1-19, 24, 28. 46-64, 86-89, 118-135, 150. 157-170. 202-219, 245-248,and 280-294 of SEQ ID NO: 1 or SEQ ID NO:2 has been replaced by a cysteine residue; and
wherein the pharmaceutical compound is chemically linked either directly or indirectly via a carrier, a cross-linker, or both a carrier and a cross-linker to the cysteine residue of the annexin variant.

5. The complex according to claim 4, wherein the convex side does not contain a cysteine residue.

6. The complex according to claim 4, wherein the pharmaceutical compound is covalently bonded to the cysteine residue of the annexin variant.

7. The complex according to claim 4, wherein the annexin variant binds to the phospholipid with a dissociation constant of approximately $10^{-6}$ M or less in the presence of $Ca^{2+}$ ions.

8. The complex according to claim 4, wherein the cross-linker is selected from the group consisting of N-succinimidyl 3-(2-pyridyldithio) propionate, N-succinimidyl maeimidoacetate, N-succinimidyl 3 -maleimidoproprionate, N-succinimidyl 4-(N-maleimidomethyl) cyclohexane-1-carboxylate, pyridyl, maleimide containing groups, halogen containing groups, an isothiocyanate, an isocyanate, an imidoester, and a succinimidylester group.

9. The complex according to claim 4, wherein the cross-linker reacts with a group other than an amino group of the pharmaceutical compound.

10. The complex according to claim 4, wherein the annexin variant and the pharmaceutical compound are in 1:1 stoichiometric ratio.

11. The complex according to claim 4, wherein the carrier is selected from the group consisting of a liposome, a dendrimer and a polymer.

12. The complex according to claim 4, wherein the pharmaceutical compound is selected from the group consisting of a therapeutic compound, and, a preventative compound.

13. The complex according to claim 12, wherein the therapeutic compound is selected from the group consisting of a toxin, an enzyme, a lipid, a carbohydrate, an immunoglobulin or a fragment thereof, an immunoconjugate, a chemotherapeutic compound, a photosensitizer, a radionuclide, a cell death inducing agent, a cell death inhibiting agent, a fibrinolytic compound, and a combination thereof.

14. The complex according to claim 13, wherein the chemotherapeutic compound is selected from the group consisting of, bleomycin, busulfan, carboplatin, carboplatinum, carmustine, cisplatin, cisplatinum, chlorambucil, 2-cholrodcoxyadenosine, cladribine, cytarabinc, cyclophosphamide, dacarbazine, daunorubicin, docetaxel, doxorubicin, etoposide, 5-fluorouracil, fludarabine, gemcitabine, hydroxyurea, idarubicin, ifosfamide, irinotecan, lomustine, meiphalan, methotrexate, mitomycin, mitoxantrone, nitrogen mustard, oxaliplatin, paclitaxel, plicamycin, procarbazine, raltitrexed, semustine, topotecan, vinbiastine, vincristine, vinorelbine, and a combination thereof.

15. The complex according to claim 12, wherein the diagnostic compound is selected from the group consisting of a fluorescent label, a contrast agent, a photosensitizer, a radionuclide, and an ultrasound agent.

16. The complex according to claim 15, wherein the fluorescent label is selected from the group consisting of fluorescein isothiocyanate, Oregon green, Alexa dyes, phycoerythrine, cyanine dyes, propidium iodide, 7-amino-actinomycin D, sytox compounds and nanocrystals.

17. The complex according to claim 16, wherein the nanocrystals are selected from the group consisting of Cadmium-Selenide, Lead-Selenide, Indium-Phosphide, and Gallium-Arsenide, and a combination thereof.

18. The complex according to claim 15, wherein the contrast agent is selected from the group consisting of gadolinium, magnetic particles, and paramagnetic particles.

19. The complex according to claim 15, wherein the photosensitizer is selected from the group consisting of phtalocyanines, rhodoporphyrins, rhodochlorins, mesorhodochlorins, phyllocrythrin and its derivatives, porphorin and its derivatives, metal- pyrollic compounds, and a combination thereof.

20. The complex according to claim 15, wherein the radionuclide is selected from the group consisting of Carbon-11, Fluorine-18, Indium-111, Iodine 123, Iodine-131, Nitrogen-13, Oxygen-15, Technetium-99m, and Zirconium-89.

21. A method of making a complex of an annexin variant and at least one pharmaceutical compound, comprising:
providing an annexin variant in which an amino acid on the concave side selected from the group consisting of amino acids at positions 1-19, 24, 28, 46-64, 86-89, 118-135, 150, 157-170, 202-219, 245-248, and 280-294 of SEQ ID NO:1 or SEQ ID NO:2 has been replaced by a cysteine residue, and chemically linking the pharmaceutical compound, either directly or indirectly via a carrier, a cross-linker, or both a carrier and a cross-linker, to the cysteine residue of the annexin variant.

22. The annexin variant according to claim 1, wherein the cysteine residue replaces an amino acid selected from the group consisting of amino acids at positions 1-19.

23. The method according to claim 21, wherein the convex side of the annexin variant does not contain a cysteine residue.

24. A complex comprising: a compound selected from the group consisting of a diagnostic compound and a research compound; and a recombinant annexin variant, wherein the annexin variant comprises a convex side that can bind with at least one phospholipid and a concave side, wherein an amino acid on the concave side selected from the group consisting of amino acids at positions 1-19, 24, 28, 46-64, 86-89, 118-135, 150, 157-170, 202-219, 245-248, and 280-294 of SEQ ID NO: 1 or SEQ ID NO:2 has been replaced by a cysteine residue; and wherein the diagnostic compound or the research compound is chemically linked either directly or indirectly via a carrier, a cross-linker, or both a carrier and a cross-linker to the cysteine-residue of the annexin variant.

25. A kit comprising:
the complex according to claim 4; and one or more further elements selected from stabilizers, buffers, labeling reagents, radionuclides, and paramagnetic compounds, wherein the said elements are in the same or a separate container than said complex.

* * * * *

SEQUENCE LISTING

<160> NUMBER OF SEQ ID NOS: 7

<210> SEQ ID NO 1
<211> LENGTH: 319
<212> TYPE: PRT
<213> ORGANISM: Homo sapiens

<400> SEQUENCE: 1

```
Ala Gln Val Leu Arg Gly Thr Val Thr Asp Phe Pro Gly Phe Asp Glu
 1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
 65                 70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Cys Gly Glu Asp Asp
305                 310                 315
```

<210> SEQ ID NO 2
<211> LENGTH: 319
<212> TYPE: PRT
<213> ORGANISM: Homo sapiens

<400> SEQUENCE: 2

```
Ala Gln Val Leu Arg Gly Thr Val Thr Asp Phe Pro Gly Phe Asp Glu
 1               5                  10                  15

Arg Ala Asp Ala Glu Thr Leu Arg Lys Ala Met Lys Gly Leu Gly Thr
             20                  25                  30

Asp Glu Glu Ser Ile Leu Thr Leu Leu Thr Ser Arg Ser Asn Ala Gln
         35                  40                  45

Arg Gln Glu Ile Ser Ala Ala Phe Lys Thr Leu Phe Gly Arg Asp Leu
     50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                 85                  90                  95

His Ala Leu Lys Gly Ala Gly Thr Asn Glu Lys Val Leu Thr Glu Ile
             100                 105                 110

Ile Ala Ser Arg Thr Pro Glu Glu Leu Arg Ala Ile Lys Gln Val Tyr
         115                 120                 125

Glu Glu Glu Tyr Gly Ser Ser Leu Glu Asp Asp Val Val Gly Asp Thr
     130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
             165                 170                 175

Ala Leu Phe Gln Ala Gly Glu Leu Lys Trp Gly Thr Asp Glu Glu Lys
         180                 185                 190

Phe Ile Thr Ile Phe Gly Thr Arg Ser Val Ser His Leu Arg Lys Val
     195                 200                 205

Phe Asp Lys Tyr Met Thr Ile Ser Gly Phe Gln Ile Glu Glu Thr Ile
     210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                 245                 250                 255

Ala Met Lys Gly Ala Gly Thr Asp Asp His Thr Leu Ile Arg Val Met
             260                 265                 270

Val Ser Arg Ser Glu Ile Asp Leu Phe Asn Ile Arg Lys Glu Phe Arg
         275                 280                 285

Lys Asn Phe Ala Thr Ser Leu Tyr Ser Met Ile Lys Gly Asp Thr Ser
     290                 295                 300

Gly Asp Tyr Lys Lys Ala Leu Leu Leu Leu Ser Gly Glu Asp Asp
305                 310                 315

<210> SEQ ID NO 3
<211> LENGTH: 319
<212> TYPE: PRT
<213> ORGANISM: Homo sapiens

<400> SEQUENCE: 3

Ala Gln Val Leu Cys Gly Thr Val Thr Asp Phe Pro Gly Phe Asp Glu
 1               5                  10                  15

Arg Ala Asp Ala Glu Thr Leu Arg Lys Ala Met Lys Gly Leu Gly Thr
             20                  25                  30

Asp Glu Glu Ser Ile Leu Thr Leu Leu Thr Ser Arg Ser Asn Ala Gln
         35                  40                  45

Arg Gln Glu Ile Ser Ala Ala Phe Lys Thr Leu Phe Gly Arg Asp Leu
```

```
                 50                  55                  60
Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                     85                  90                  95

His Ala Leu Lys Gly Ala Gly Thr Asn Glu Lys Val Leu Thr Glu Ile
                    100                 105                 110

Ile Ala Ser Arg Thr Pro Glu Glu Leu Arg Ala Ile Lys Gln Val Tyr
                115                 120                 125

Glu Glu Glu Tyr Gly Ser Ser Leu Glu Asp Asp Val Val Gly Asp Thr
            130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
        210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
            290                 295                 300

Gly Asp Tyr Lys Lys Ala Leu Leu Leu Leu Ser Gly Glu Asp Asp
305                 310                 315

<210> SEQ ID NO 4
<211> LENGTH: 319
<212> TYPE: PRT
<213> ORGANISM: Homo sapiens

<400> SEQUENCE: 4

Ala Gln Val Leu Arg Gly Cys Val Thr Asp Phe Pro Gly Phe Asp Glu
  1               5                  10                  15

Arg Ala Asp Ala Glu Thr Leu Arg Lys Ala Met Lys Gly Leu Gly Thr
                 20                  25                  30

Asp Glu Glu Ser Ile Leu Thr Leu Leu Thr Ser Arg Ser Asn Ala Gln
             35                  40                  45

Arg Gln Glu Ile Ser Ala Ala Phe Lys Thr Leu Phe Gly Arg Asp Leu
         50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                     85                  90                  95

His Ala Leu Lys Gly Ala Gly Thr Asn Glu Lys Val Leu Thr Glu Ile
                    100                 105                 110
```

```
Ile Ala Ser Arg Thr Pro Glu Glu Leu Arg Ala Ile Lys Gln Val Tyr
            115                 120                 125

Glu Glu Glu Tyr Gly Ser Ser Leu Glu Asp Asp Val Val Gly Asp Thr
        130                 135                 140

Ser Gly Tyr Tyr Gln Arg Met Leu Val Val Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
            195                 200                 205

Phe Asp Lys Tyr Met Thr Ile Ser Gly Phe Gln Ile Glu Glu Thr Ile
            210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
            275                 280                 285

Lys Asn Phe Ala Thr Ser Leu Tyr Ser Met Ile Lys Gly Asp Thr Ser
            290                 295                 300

Gly Asp Tyr Lys Lys Ala Leu Leu Leu Leu Ser Gly Glu Asp Asp
305                 310                 315

<210> SEQ ID NO 5
<211> LENGTH: 319
<212> TYPE: PRT
<213> ORGANISM: Homo sapiens

<400> SEQUENCE: 5

Ala Gln Val Leu Arg Gly Thr Val Cys Asp Phe Pro Gly Phe Asp Glu
  1               5                  10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
            115                 120                 125

Glu Glu Glu Tyr Gly Ser Ser Leu Glu Asp Asp Val Val Gly Asp Thr
        130                 135                 140

Ser Gly Tyr Tyr Gln Arg Met Leu Val Val Leu Gln Ala Asn Arg
145                 150                 155                 160

Asp Pro Asp Ala Gly Ile Asp Glu Ala Gln Val Glu Gln Asp Ala Gln
                165                 170                 175
```

```
Ala Leu Phe Gln Ala Gly Glu Leu Lys Trp Gly Thr Asp Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
        210                 215                 220

Asp Arg Glu Thr Ser Gly Asn Leu Glu Gln Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
        290                 295                 300

Gly Asp Tyr Lys Lys Ala Leu Leu Leu Leu Ser Gly Glu Asp Asp
305                 310                 315
```

<210> SEQ ID NO 6
<211> LENGTH: 319
<212> TYPE: PRT
<213> ORGANISM: Homo sapiens

<400> SEQUENCE: 6

```
Ala Gln Val Leu Arg Gly Thr Val Thr Asp Cys Pro Gly Phe Asp Glu
  1               5                  10                  15

Arg Ala Asp Ala Glu Thr Leu Arg Lys Ala Met Lys Gly Leu Gly Thr
             20                  25                  30

Asp Glu Glu Ser Ile Leu Thr Leu Leu Thr Ser Arg Ser Asn Ala Gln
         35                  40                  45

Arg Gln Glu Ile Ser Ala Ala Phe Lys Thr Leu Phe Gly Arg Asp Leu
     50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                 85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
        210                 215                 220

Asp Arg Glu Thr Ser Gly Asn Leu Glu Gln Leu Leu Ala Val Val
```

```
                        225                 230                 235                 240
Lys Ser Ile Arg Ser Ile Pro Ala Tyr Leu Ala Glu Thr Leu Tyr Tyr
                    245                 250                 255

Ala Met Lys Gly Ala Gly Thr Asp Asp His Thr Leu Ile Arg Val Met
                260                 265                 270

Val Ser Arg Ser Glu Ile Asp Leu Phe Asn Ile Arg Lys Glu Phe Arg
            275                 280                 285

Lys Asn Phe Ala Thr Ser Leu Tyr Ser Met Ile Lys Gly Asp Thr Ser
        290                 295                 300

Gly Asp Tyr Lys Lys Ala Leu Leu Leu Leu Ser Gly Glu Asp Asp
305                 310                 315

<210> SEQ ID NO 7
<211> LENGTH: 319
<212> TYPE: PRT
<213> ORGANISM: Homo sapiens

<400> SEQUENCE: 7

Ala Cys Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
                100                 105                 110

Ile Ala Ser Arg Thr Pro Glu Glu Leu Arg Ala Ile Lys Gln Val Tyr
            115                 120                 125

Glu Glu Glu Tyr Gly Ser Ser Leu Glu Asp Asp Val Val Gly Asp Thr
        130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285
```

-continued

```
Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Ser Gly Glu Asp Asp
305             310                 315
```